US010905397B2

(12) United States Patent
Yang et al.

(10) Patent No.: US 10,905,397 B2
(45) Date of Patent: Feb. 2, 2021

(54) ARRAY TRANSDUCER-BASED SIDE-SCANNING PHOTOACOUSTIC-ULTRASONIC ENDOSCOPE

(71) Applicant: UNIST(ULSAN NATIONAL INSTITUTE OF SCIENCE AND TECHNOLOGY), Ulsan (KR)

(72) Inventors: Joon Mo Yang, Ulsan (KR); Chae Un Kim, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 443 days.

(21) Appl. No.: 15/872,414

(22) Filed: Jan. 16, 2018

(65) Prior Publication Data
US 2018/0228464 A1 Aug. 16, 2018

(30) Foreign Application Priority Data

Feb. 15, 2017 (KR) ........................ 10-2017-0020710

(51) Int. Cl.
A61B 8/00 (2006.01)
A61B 5/00 (2006.01)
A61B 8/12 (2006.01)
A61B 8/08 (2006.01)

(52) U.S. Cl.
CPC .......... A61B 8/4416 (2013.01); A61B 5/0062 (2013.01); A61B 5/0073 (2013.01); A61B 5/0084 (2013.01); A61B 5/0095 (2013.01); A61B 8/12 (2013.01); A61B 8/4483 (2013.01);
(Continued)

(58) Field of Classification Search
CPC ..... A61B 8/4416; A61B 5/002; A61B 5/0073; A61B 8/12; A61B 8/4483; A61B 5/0084; A61B 5/0095; A61B 8/5246; A61B 8/5269; A61B 8/483; A61B 8/4494; A61B 8/4477
See application file for complete search history.

(56) References Cited

U.S. PATENT DOCUMENTS 4,543,960 A  10/1985 Harui et al.
4,982,724 A  1/1991 Saito et al.
5,125,411 A  6/1992 Yokoi et al.
(Continued)

FOREIGN PATENT DOCUMENTS

JP  2012-050607  3/2012
JP  2012-228401  11/2012
(Continued)

OTHER PUBLICATIONS

Korean Intellectual Property Office, Office Action, dated Jun. 15, 2018, in Republic of Korea Patent Application No. 10-2017-0020710.
(Continued)

Primary Examiner — Sanjay Cattungal
(74) Attorney, Agent, or Firm — Klarquist Sparkman, LLP

(57) ABSTRACT

A photoacoustic-ultrasonic (i.e. dual mode) endoscope includes: an optical fiber; a light diffuser configured to diffuse a laser beam delivered through the optical fiber to a target point of an object to be examined; and an array transducer through which the diffused laser beam passes and configured to generate ultrasonic waves or detect ultrasonic waves generated in the object to be examined.

19 Claims, 14 Drawing Sheets

(52) U.S. Cl.
CPC ............. *A61B 8/483* (2013.01); *A61B 8/5246* (2013.01); *A61B 8/5269* (2013.01)

(56) References Cited

U.S. PATENT DOCUMENTS

| | | | | |
|---|---|---|---|---|
| 5,353,262 | A * | 10/1994 | Yakymyshyn | ........... G01H 9/00 340/566 |
| 5,530,780 | A * | 6/1996 | Ohsawa | ................. A61B 18/24 385/31 |
| 8,454,512 | B2 * | 6/2013 | Wang | ................. G01N 29/0681 600/437 |
| 8,758,251 | B2 | 6/2014 | Kohno | |
| 8,849,079 | B2 | 9/2014 | Yoshida et al. | |
| 8,932,223 | B2 | 1/2015 | Emelianov et al. | |
| 9,351,646 | B2 | 5/2016 | Irisawa | |
| 9,662,020 | B2 * | 5/2017 | Irisawa | ................ A61B 5/0095 |
| 9,730,587 | B2 * | 8/2017 | Herzog | .............. G01N 29/2418 |
| 9,924,925 | B2 | 3/2018 | Fujimura | |
| 10,342,435 | B2 | 7/2019 | Irisawa et al. | |
| 2002/0105250 | A1 * | 8/2002 | Klee | ..................... H01L 41/319 310/365 |
| 2006/0238067 | A1 * | 10/2006 | Dausch | ................. B06B 1/0622 310/311 |
| 2007/0206193 | A1 * | 9/2007 | Pesach | ................. A61B 5/0095 356/432 |
| 2008/0004686 | A1 * | 1/2008 | Hunt | ..................... A61F 2/2475 623/1.11 |
| 2011/0021924 | A1 | 1/2011 | Sethuraman et al. | |
| 2011/0201973 | A1 * | 8/2011 | Stephens | ................. A61B 8/08 601/2 |
| 2012/0275262 | A1 * | 11/2012 | Song | .................... A61B 5/0095 367/7 |
| 2014/0051967 | A1 * | 2/2014 | Irisawa | ................... A61B 1/07 600/407 |
| 2014/0360273 | A1 * | 12/2014 | Zhang | ................ G01N 29/2418 73/643 |
| 2017/0000353 | A1 * | 1/2017 | Li | ........................ A61B 5/0075 |

FOREIGN PATENT DOCUMENTS

| | | |
|---|---|---|
| JP | 5856032 | 2/2016 |
| JP | 6064098 | 5/2017 |
| KR | 10-2014-0126554 | 10/2014 |

OTHER PUBLICATIONS

Bell, K.L., et al., "Integrated Transrectal Probe for Translational Ultrasoundphotoacoustic Imaging," SPIE BiOS, 2016.

Dietrich, C., "Endoscopic Ultrasound: An Introductory Manual and Atlas", Thieme Stuttgart-New York, 2006.

Hanrath, P., et al., "Transesophageal Horizontal and Sagittal Imaging of the Heart with a Phased Array System. Initial Clinical Results," Cardiovascular Diagnosis by Ultrasound, Martinus Nijoff Publishers, The Hague, 1982, Chapter 31, pp. 280-281.

Laser Institute of America, "American National Standard for Safe Use of Lasers," ANSI Z136.1-2007.

Oraevsky, A.A., et al., "Laser Optoacoustic Tomography of Layered Tissues: Signal Processing," SPIE vol. 2979, pp. 59-70.

Tsyboulski, D., et al., "Dual Modality Optoacoustic and Laser Ultrasound Endoscopy System," Proc. of SPIE vol. 8943, pp. 89432S-1-5.

Wygant, I.O., et al., "Integrated Ultrasound Imaging Systems Based on Capacitive Micromachined Ultrasonic Transducer Arrays," IEEE 2008, pp. 704-707.

Yang, J.-M., et al., "Simultaneous Functional Photoacoustic and Ultrasonic Endoscopy of Internal Organs In Vivo," Nature Medicine, 18(8), Aug. 2012, pp. 1297-1303.

Yang, J.-M., et al., "Photoacoustic Endoscopy," Optics Letters, 34(10), May 15, 2009, pp. 1591-1593.

Yuan, Y., et al., "Preclinical Photoacoustic Imaging Endoscope Based on Acousto-Optic Coaxial System Using Ring Transducer Array," Optics Letters, 35(13), Jul. 1, 2010, pp. 2266-2268.

Notice of Allowance dated Jun. 19, 2019, issued in related Korean Application No. 10-2017-0020710 (6pps).

* cited by examiner

PRIOR DOCUMENT 9

PRIOR DOCUMENT 11

PRIOR DOCUMENT 12

PRIOR DOCUMENT 14

PRIOR DOCUMENT 13

PRIOR DOCUMENT 15

ARRAY TRANSDUCER-BASED SIDE-SCANNING PHOTOACOUSTIC-ULTRASONIC ENDOSCOPE

CROSS-REFERENCE TO RELATED APPLICATION

This application claims the benefit of Korean Patent Application No. 10-2017-0020710, filed on Feb. 15, 2017, in the Korean Intellectual Property Office, the disclosure of which is incorporated herein in its entirety by reference.

BACKGROUND

1. Field

One or more of the embodiments of the present disclosure relate to a medical tomographic endoscopic apparatus that has a probe that is long and slender, like the current endoscopic ultrasound (EUS) probes utilized in clinics, wherein the endoscopic apparatus is inserted into an object to be examined and provides a tomographic image of the interior thereof. The main objective of the present disclosure is to provide new system concepts and detailed probe structures to enable large-depth imaging that approaches the theoretical limit according to the imaging principle of photoacoustic tomography (PAT), wherein a restricted probe size (or optical illumination area) is also under a premise. Moreover, to enable rapid capturing of two-dimensional (2D) or three-dimensional (3D) tomographic images for the single shot of a laser pulse, all the embodiments are designed to operate based on the array transducer-based ultrasonic signal detection mechanism, which is typically utilized in conventional EUS technology. The engagement of such an array transducer also implies that the proposed endoscopic systems may be utilized for dual-mode photoacoustic and ultrasonic imaging. The presented endoscopic systems are mainly intended to be used for imaging the gastrointestinal (GI) tract; however, they may also be applied for imaging its adjacent organs, such as the heart, pancreas, and prostate, similar to conventional ultrasound-based endoscopic or minimally-invasive imaging techniques, such as transesophageal echocardiography (TEE) or transrectal ultrasound (TRUS).

2. Description of the Related Art

The present disclosure relates to a range of tomographic endoscopic systems that can provide cross-sectional or volumetric images of target tissue based on the general principle of photoacoustic endoscopy (PAE) or optoacoustic endoscopy (OAE) (see Prior Documents 7 and 8), and conventional EUS (see Prior Document 1) by consolidating the relevant functions in a single device. The proposed endoscopic systems are intended to be used for a variety of medical procedures, such as the diagnosis of digestive diseases or cardiovascular diseases, by using an ultrasonic array transducer as the core part of the proposed systems, like the current array transducer-based EUS probes utilized in clinics (see Prior Documents 1-6).

The general principle of EUS is already well known and well established, and it is currently being utilized in clinical settings. However, PAE refers to the novel tomographic endoscopic technique that embodies PAT or photoacoustic imaging (PAI) technique in a small probe. In an illustrative imaging procedure, a probe with a small diameter is inserted into an object to be examined. Electromagnetic waves with a very short pulse width (usually less than 1 μs) are instantly applied to the region of interest to generate acoustic waves, which are typically referred to as photoacoustic waves, and a tomographic image of the interior of the biological tissue is produced by obtaining (i.e., scanning) the generated photoacoustic signals over the region of interest.

Although the photoacoustic effect through which electromagnetic waves are applied to a target object and converted into acoustic waves has been known since the 1880s, it was not until the early of 1990s that the first photoacoustic image was actually obtained from real biological tissue based on the photoacoustic effect. At that time, the advent of commercial pulsed-light sources, such as the Q-switched laser, played a crucial role in the breakthrough; from then on, various types of PAI systems have been developed with a greater range of medical applicability. In general, a technique that can provide a tomographic image of the interior of biological tissue based on the photoacoustic effect is referred to as PAT or PAI.

The reason that PAT is currently in the medical imaging spotlight is because it is capable of providing a new type of medically useful image information that is not possible to obtain with conventional medical imaging techniques, such as magnetic resonance imaging, X-ray computed tomography, positron emission tomography, and ultrasonography. Furthermore, it is widely accepted that PAT is very excellent, in terms of imaging depth, spatial resolution, imaging speed, and safety, all of which are critical factors for actual clinical use.

An objective of the present disclosure is to apply the PAT technique's benefits to endoscopy or minimally-invasive imaging, and more concretely, to solve many of the limitations and problems of existing array transducer-based PAE probes, such as low imaging depths and large probe size issues, thereby to more effectively apply related technology to GI endoscopy, cardiology, urology, etc.

Like more well-known or more general PAT systems (that are not limited to endoscopy), a PAE system also requires three core system elements: a light source that generates an electromagnetic pulse (typically in the visible wavelength range), an imaging probe that approaches an object to be examined and acquires a series of photoacoustic signals, and a data processor and displayer that process the acquired photoacoustic signals and provide the processed photoacoustic image to a user. However, the shape and size of the imaging probe is the most important and distinguishable technical requirement for the specific application area called "endoscopy"; the probe should be long, and its diameter should be very small or narrow (i.e., with a thickness equal to or less than a predetermined value).

After the first conceptual suggestion of PAE by Oraevsky et al. (1997), as described in Prior Document 8, in which the imaging probe was referred to as an "optoacoustic endoscope", a number of PAE probes have been developed to address technical requirements, such as "probe miniaturization" and "specifying a device configuration or operation principle for endoscopy." However, no commercially successful or clinically applicable PAE system has yet been developed that satisfies both of these technical requirements due to many underlying technical challenges. The most well-known and difficult challenge is that, in order to successfully create a working PAE probe, all the optical and acoustical elements should be effectively integrated and arranged in a small and restricted space; an adequate scanning mechanism, through which a tomographic image can be produced, should also be developed and integrated into the device.

Accordingly, the main purpose of the present disclosure is to provide a concept for an advanced PAE system or probe structure that may satisfy the aforementioned technical requirements and allow an imaging probe to be more smoothly inserted into an object to be examined and provide a photoacoustic image with much higher quality than those of prior inventions, even from a deep inside of the object to be examined.

Although there is a clear difference between the principles of PAE and EUS, in which a PAE image is produced through the unique energy transduction mechanism that converts pulsed electromagnetic waves into acoustic waves, PAE is still very closely related to conventional EUS (see Prior Document 1). This is because all of the signals required to produce a PAE image are acquired by means of acoustic waves. This means that, in some respects, a PAE device can be understood as a device in which the functions that guide and emit laser beam (or electromagnetic waves) are added to the typical system composition of a conventional EUS device. Due to these system characteristics, most PAE systems may be able to provide both a photoacoustic image and a conventional ultrasound image.

Hence, considering only the methods of ultrasound signal detection other than those that deliver and emit electromagnetic waves (e.g., a laser beam in general) to an object to be examined, any of the single-element ultrasonic transducer-based mechanical scanning mechanisms or array transducer-based electronic scanning mechanisms currently being utilized in clinical EUS instruments may also be utilized in a PAE probe (see Prior Document 1). The advantages and disadvantages of the mechanical and the electronic scanning mechanisms will be briefly explained in the following section.

First, the main advantage of the single-element ultrasonic transducer-based mechanical scanning mechanism is that it may be possible to fabricate a very small or slender-shaped probe because the space occupied by the single transducer is not very large. Moreover, the costs for implementing the related instruments are relatively low. However, the main drawback of the mechanical scanning mechanism is that, since a single-element ultrasonic transducer that can receive the signals that are bounced back only from the aiming direction of the transducer surface is mounted on the scanning tip of an endoscopic probe, in order to obtain a 2D image or a 3D image, a series of processes that emit a laser pulse, and then detect the generated photoacoustic waves, should be repeatedly performed by changing the physical position or the aiming direction of the ultrasonic transducer (e.g., rotational scanning in general). Due to the aforementioned advantages and disadvantages, in the current EUS technology utilized in clinics, the mechanical scanning mechanism is mostly applied to ultra-small endoscopic devices with probe diameters ranging from ~1 mm to ~3 mm, such as intravascular ultrasound (IVUS) catheter probes, which are manufactured for introduction into blood vessels, or EUS mini-probes, which are manufactured to be inserted into the instrument channels or the accessory channels of a video endoscope (of course, an EUS instrument does not require a laser pulse guiding and emitting function).

In contrast, the array transducer-based electronic scanning mechanism differs from the mechanical scanning mechanism in the following ways. First, its major drawback is that it is relatively more difficult to reduce the size of the related endoscopic probe than the size of the mechanical scanning mechanism because it employs multiple transducer elements to detect ultrasound waves. Thus, problems, such as cross-talk or signal interference between channels, may occur and the cost of implementing the system may also be high. However, the electronic scanning mechanism has the following unique advantage over the mechanical scanning mechanism. That is, as the word "array" says, all of the one-dimensional signals (i.e., A-lines) required to produce a 2D or 3D tomographic image can be simultaneously obtained through the plurality of detection channels formed in an array transducer by only using a single shot of a laser pulse. This means that, without making any change to the sensor or probe position, a tomographic image covering a desired range of the target object may be acquired at one time, after just one laser pulse firing process. Consequently, in the current EUS technology utilized in clinics, the electronic scanning mechanism is mostly applied to EUS probes that are manufactured for the diagnosis of digestive diseases, for which high-level probe miniaturization is unnecessary.

In addition to the rapid scanning capability of the electronic scanning mechanism, another important merit of an array transducer in endoscopy is that an image display style and a field of view may be arbitrarily chosen, depending on the application direction, by appropriately changing the arrangement pattern of the ultrasonic senor elements (i.e., array pattern) and their expansion range. Thus, various types of array probes have been developed and utilized in the current EUS technology, and they are typically classified into a side-scanning linear array probe, a side-scanning radial array probe, and a forward-scanning array probe depending on the arrangement pattern or scanning direction (see Prior Document 1).

Due to the aforementioned advantages and disadvantages of each of the scanning mechanisms, various PAE systems that adopt either of these two scanning mechanisms have been suggested, to date. Among them, representative examples of prior technologies that have adopted the array transducer-based electronic scanning mechanism (as also pursued by the present disclosure) include those presented in Prior Document 9 ($4^{th}$ IEEE Conference on Sensors 1&2, 704(2005)), Prior Document 10 (Optics Letters 35(13), 2266(2010)), Prior Document 11 (US Patent Application Publication No. 2011-0021924), Prior Document 12 (U.S. Pat. No. 8,932,223), Prior Document 13 (Proc. of SPIE 8943, 89432S(2014)), Prior Document 14 (Korean Patent Application Publication No. 2014-0126554), and Prior Document 15 (Proc. of SPIE 9708, 97080A(2016)).

Therefore, all the endoscopic systems disclosed in the prior documents haveadopted a common system composition in which an array transducer is employed as the core part of acoustic signal detection, like conventional array transducer-based EUS probes, and then an optical fiber or illumination unit is placed around the array transducer to deliver laser light to the target tissue for PAI (note that the addition of the optical fiber is the major difference between a PAE probe and an EUS probe). However, there are obvious differences in the pattern of the employed array transducer, the detailed configuration between the array transducer and the light illumination unit placed around the array transducer, and the level of system realization. Detailed features of the prior systems will now be briefly reviewed and discussed with reference to FIGS. 12 through 16.

First, Prior Document 9, whose system is illustrated in FIG. 12, might be the first document that proposes the concept that applies an ultrasonic "array transducer" to PAE. Moreover, this document disclosed a new type of an ultrasonic array sensor that can be fabricated like the typical mass production process of a semiconductor integrated circuit. However, Prior Document 9 only mentioned the possibility of applying this array sensor to PAE or intravascular imaging; it does not disclose any detailed shape or structure of a PAE probe or the associated implementation methods. Thus, the information presented in Prior Document 9 only focused on demonstrating the operation capability of the ultrasonic array sensor by performing a couple of phantom experiments.

However, in Prior Documents 10 through 15, more detailed system concepts or real embodiment results for a PAE application were disclosed in which related endoscopic probes started to have a more endoscope-like appearance; to some extent, these documents also addressed probe miniaturizations, which have the following features.

First, the endoscopic system disclosed in Prior Document 10 has a structure that detects photoacoustic signals by using a ring type array transducer comprised of 64 elements, which are symmetrically placed around the central axis of the endoscope, and the light energy required for photoacoustic signal generation is delivered via a cone shape reflection mirror, which also is placed at the central axis of the endoscope next to the array transducer. However, the endoscopic system as is may not be applicable to a clinical endoscopic procedure because its probe is still too big (9 cm in length and 3 cm in diameter), and the glass material utilized for the probe encapsulation is not suitable for actual clinical use in terms of safety. Although its size could be reduced further, any detailed method or probe structure for how to reduce the probe size is not disclosed in Prior Document 10. Moreover, the endoscopic system of Prior Document 10 has a drawback in that a light emitting area (LEA) and an ultrasonic sensor area (USA) are spaced apart from each other (the problem caused by such an arrangement will be explained later).

Prior Documents 11 and 12 present a couple of probe structures that can realize an intravascular PAE device by using an existing IVUS catheter probe. For example, Prior Document 11 presents information on a PAE probe constructed by employing an existing array transducer-based IVUS catheter probe as the basic frame of the probe, and multiple optical fibers are then placed at predetermined intervals around the surface of the catheter to enable photoacoustic imaging. However, the proposed structure has a disadvantage in that, since a limited number of optical fibers are simply added to the outer surface of an existing array transducer-based IVUS catheter, the intensity of light illumination may not be uniform over the 360° scan area, and the probe's flexibility may not be good enough. The non-uniformity issue of light illumination could be solved by placing optical fibers with a narrower diameter more densely. However, in this case, the probe flexibility may be seriously decreased in proportion to the total number of optical fibers that are used.

Prior Document 13, whose system is illustrated in FIG. 16, presents another typeof PAE probe with an actual embodiment result like the case shown in Prior Document 10. The major part of this work appears to be in the probe miniaturization result that achieved a diameter of 13.9 mm and a length of 60 mm, which are much smaller than those in the case discussed in Prior Document 10. However, the endoscopic probe presented in Prior Document 13 has a disadvantage in that, since the probe has a structure that obtains a photoacoustic signal by using only an 8-element-based array transducer, which is placed facing the distal end of the probe, a parabolic mirror, which has a 45°-tilted reflection surface and faces that array transducer, has to mechanically rotate in order to obtain a photoacoustic image over a desired scan range. Thus, the suggested scanning mechanism may not be a desirable direction for actual clinical use because the main purpose of using this type of array transducer is to avoid any mechanically moving component inside an endoscopic probe.

The endoscopic system disclosed in Prior Document 14 also has a similar feature that adopts the combined electronic and mechanical scanning mechanism of an ultrasonic array transducer and a scanning mirror, like the case shown in Prior Document 13. Therefore, its image scanning process is fully accomplished by the additional mechanical scanning process provided by the scanning mirror. However, as mentioned above (Prior Document 13), the core benefit of employing an array transducer was not fully utilized, and the mismatch issue between an LEA and a USA still exists in this endoscopic system.

The endoscopic systems disclosed in Prior Document 15 relate to a rigid probe developed for the diagnosis of prostate diseases via an anus insertion, i.e., transrectal imaging of the prostate. In an embodiment, a 192-element-based array transducer and a couple of optical fibers distributed around the array transducer are commonly placed facing the same direction on the same side of the probe to perform side-scanning. The main difference between this endoscopic probe and the previous endoscopic systems is that the employed array transducer is a linear type array transducer. In Prior Document 15, in addition to presenting the explained actual probe embodiment result, another probe design with a different configuration of optical illumination unit was also presented. However, in any case, the endoscopic structures presented in Prior Document 15 have the limitation that the LEA of an endoscopic probe is limited to the surrounding area of an array transducer or several spots that are discontinuously distributed around a linear array transducer. That is, the endoscopic probes also have a similar structure in that an LEA and a USA are completely separate from each other. This limitation was probably caused because the authors of Prior Document 15 only focused on a PAE probe embodiment by using an existing commercial ultrasonic array transducer, rather than focusing on working out an ideal probe structure that enables a uniform light illumination to an object to be examined over the entire area where the transducer elements are distributed. For reference, although not described in detail, an end portion of the probe that is actually implemented appears to be quite long, and it is described that its diameter is about 25 mm.

Until now, several key features of representative prior inventions that use an array transducer as a component for detecting a photoacoustic signal have been described. Although some other documents have also suggested PAE probes that have been developed based on a similar array transducer-based signal detection mechanism, those inventions did not describe the detailed shapes and structures of the endoscopes; thus, a detailed explanation was not given (for reference, Prior Document 8, which was published in 1997, was the first to suggest the endoscopic application of PAT by combining an ultrasonic detector and an optical illumination unit).

All the PAE probes disclosed in Prior Documents 10 through 15 can be classified as array transducer-based side-scanning endoscopic probes; among them, only the endoscopic probe shown in Prior Document 15 utilized a linear array transducer-based side-scanning mechanism as pursued by the present disclosure; however, the main application target of that probe is different from the current disclosure. Setting aside the additional future tasks that are required to achieve further miniaturizations of those endoscopic probes, which is actually the first thing that should be solved for a successful clinical translation, all of the endoscopic systems disclosed in Prior Documents 10 through 15 have the following fundamental drawbacks.

When any of the previous light illumination methods is utilized for a PAE probe, an optical illumination area (IA) formed inside an object and an ultrasonic scan area (SA) formed inside the object by the collective works of the sensor elements that constitute an array transducer do not perfectly coincide. This occurs because, in most of the above-described prior inventions, light illumination units are simply added at some specific positions around a ready-made array transducer, which is actually manufactured for conventional ultrasound imaging rather than for PAE; thus, an LEA and a USA are arranged separately. This leads to the following problem: light energy is not uniformly delivered over the entire scan area (i.e., SA) of an array transducer during its scanning process, so a dead zone occurs in an acquired photoacoustic image. For example, in the endoscopes disclosed in Prior Documents 10, a laser beam coincides with an ultrasonic scan plane formed by an array transducer only at a specific position (or radial distance) from the probe.

If any of the illumination methods suggested by the above inventions is utilized for a PAE probe, the discrepancy between an LEA and a USA may increase as the size of an array transducer (or a scan head) increases. In order to avoid this problem, one possible option would be to reduce the entire size of the scan head. However, if the size of a scanning head is reduced while maintaining this type of an arrangement structure, one serious effect is that the maximum imaging depth of the PAE probe may be greatly reduced because the total available space for the scan head still has to be divided into the two compartments, i.e., an LEA and a USA, as the arrangement structure is preassumed. Here, the imaging depth decrease effect is also closely related to the maximally allowable light dose issue in accordance with the laser safety regulation described in the next section. It is true that, in prior inventions, an LEA is limited only to specific positions so the total amount of light energy that is actually delivered to an object to be examined may be significantly limited.

In general, the main purpose for using such an array transducer is to maximize the imaging performance in terms of imaging depth and imaging speed, rather than to facilitate probe miniaturization. Therefore, reducing the size of the probe may not be a desirable way to solve the aforementioned discrepancy issue.

Taken together, an array transducer-based RAE probe may be understood as a photoacoustic version of an array transducer-based EUS probe, which is currently utilized in clinics. This is a plausible comparison because, even in the PAE probe, although an optical illumination unit capable of transferring light energy to an object to be examined needs to be added, an ultrasonic array transducer is still a key element, just as it is in a conventional EUS probe.

In this regard, it is true that the above-described prior inventions, as well as any other similar apparatus that appropriately combines these two key elements, may have the potential to be used as a PAE probe if a certain level of probe miniaturization is achieved. However, in order to realize a useful endoscopic system that could be utilized in actual clinics, it is necessary to derive an optimal structure of an optimal light illumination unit and an ultrasonic detection unit that can maximize the imaging performance within a restricted probe size, which is actually the point that the present disclosure aims to address.

PRIOR DOCUMENTS

Patent Documents

Prior Document 3: U.S. Pat. No. 4,543,960 (Oct. 1, 1985)
Prior Document 4: U.S. Pat. No. 4,982,724 (Jan. 8, 1991)
Prior Document 5: U.S. Pat. No. 5,125,411 (Jun. 30, 1992)
Prior Document 6: U.S. Pat. No. 8,758,251 (Jun. 24, 2014)
Prior Document 11: US Patent Application Publication No. 2011-0021924 (2011.01.27.)
Prior Document 12: U.S. Pat. No. 8,932,223 (Jan. 13, 2015)
Prior Document 14: Korean Patent Application Publication No. 2014-0126554 (Oct. 31, 2014)

Non-Patent Documents

Prior Document 1: Dietrich, C. Endoscopic Ultrasound: An Introductory Manual and Atlas, (Thieme, New York, 2006)
Prior Document 2: P. Hanrath et al., Chapter 31: "Transesophageal Horizontal and Sagittal Imaging of the Heart with a Phased Array System, Initial Clinical Results," in the book "Cardiovascular Diagnosis by Ultrasound," pp 280-288 (1982)
Prior Document 7: J M Yang, et al., "Photoacoustic endoscopy," Optics Letters 34(10), 1591 (2009)
Prior Document 8: Oraevsky, et al., "Laser optoacoustic tomography of layered tissues: signal processing," Proc. SPIE, 2979, 59 (1997)
Prior Document 9: I O Wygant, et al., "Integrated ultrasound imaging systems based on capacitive micromachined ultrasonic transducer arrays," $4^{th}$ IEEE Conference on Sensors Vol. 1&2, 704 (2005)
Prior Document 10: Y Yuan, et al., "Preclinical photoacoustic imaging endoscope based on acousto-optic coaxial system using ring transducer array," Optics Letters 35(13), 2266 (2010)
Prior Document 13: D Tsyboulski, et al., "Dual modality optoacoustic and laser ultrasound endoscopy system," Proc. of SPIE 8943, 89432S (2014)
Prior Document 15: K L Bell, et al., "Integrated transrectal probe for translational ultrasound-photoacoustic imaging," Proc. of SPIE 9708, 97080A (2016)
Prior Document 16: Laser Institute of America, *American National Standard for Safe Use of Lasers*, ANSI Z136.1-2007, American National Standards Institute, Inc., New York (2007)
Prior Document 17: J M Yang, et al., "Simultaneous functional photoacoustic and ultrasonic endoscopy of internal organs in vivo," Nature Medicine 18(8), 1297 (2012)

SUMMARY

As mentioned above, the present disclosure relates to an array-transducer-based side-scanning PAE probe and system, and a main objective of the present disclosure is to provide a more advanced endoscopic structure that does not suffer from the mismatch issue between an optical illumination area (IA) and an ultrasonic scan area (SA) that exists in the prior inventions. More specifically, the present disclosure aims to work out a novel PAE probe structure with an imaging performance that is significantly better than that of existing PAE probes, especially in terms of imaging depth, by using an array transducer as a signal detector in order to utilize the PAE probe to diagnose digestive diseases or heart diseases via a GI tract introduction.

First, the reasons why the probe structures suggested in the prior inventions described above have fundamental limits for use in GI endoscopy and are unable to achieve a large-depth imaging will be explained from a general technical viewpoint along with several key requirements that must be considered when designing a clinical endoscope.

In order to design a clinical endoscope, a specific application direction of the endoscope or a specific target object to be imaged must first be determined. This is important because basic specifications, such as the shape and the size of the endoscope, need to be determined first depending on the set application direction. In other words, unlike other general PAI systems (i.e., a non-endoscopic system), it is very important to find an effective structure because the available space of an imaging probe is very limited, and the effective probe structure or the main focus of a probe design may also vary depending on the application direction.

In the general video endoscopes and EUS probes utilized for clinical GI endoscopy, the diameter of the hose portion inserted into the human body typically ranges from ~1 cm to ~1.3 cm in order for the hose portion to be inserted into a digestive tract, such as the esophagus or the large intestine, without much difficulty. However, in order to add a probe steering function to those hose portions, such as the probe angulation capability, it is necessary to install a related unit at a point that is as close as possible to the distal end of a hose. This means that better probe steering performance can be achieved as the total length of a scanning head section, which is typically inflexible and in which an array transducer is installed, decreases.

If the scanning head section is too short, the space where an array transducer is to be installed is also reduced; consequently, the spatial angle (or the solid angle) for detecting the photoacoustic waves propagating from a signal source also decreases. This is similar to the well-known principle, known as the "limited-view problem", which is frequently discussed in conventional ultrasonography.

These two requirements conflict with each other; thus, an appropriate trade-off must be found when designing a probe. In the current array transducer-based EUS technology utilized for clinical GI endoscopy, for example, a related endoscopic probe is manufactured so that the length of the rigid scanning head section is equal to or less than ~3 cm, considering all these requirements.

Therefore, if a PAE probe is designed to be used like an existing array transducer-based EUS probe inserted into a GI tract, both an array transducer and a light illumination unit needed for PAI have to be installed in a space provided by the scanning head size with a diameter of 1.3 cm or less and a length of about 3 cm.

If the discussed PAE probe must also have large-depth imaging performance, like existing array transducer-based EUS probes, the aforementioned size issue makes the situation even more difficult. This is because, in order to achieve large-depth imaging, a sufficient amount of light energy has to be delivered to an object to be examined, but the total area available for light illumination, which can be simply calculated by subtracting the area needed for the array transducer from the entire area (i.e., ~1.3 cm×3 cm) formed on the outer surface of the scanning head section, is significantly reduced.

In biomedical photoacoustics, it is well-known that the maximum imaging depth of a PAI system is mostly affected by the light illumination parameters rather than the sensitivity of an employed ultrasonic transducer. This is because the optical fluence distribution ($\Phi(r)$) of the photons inside a biological tissue (where the optical fluence [J/m$^2$] is defined as the energy flow of the photons per unit area regardless of the flow direction in a steady-state) shows a more sharp decay due to rapid optical diffusion, as shown in Formula 1, than the amplitude ($A(z)$) of the acoustic waves traveling in biological tissue (Formula 2).

$$\Phi(r) \propto \frac{e^{-\mu_{eff} r}}{r} \quad (1)$$

$$A(z, f) = A_0 e^{-a f^b z/8.7} \quad (2)$$

For example, according to the two formulas, acoustic waves with a center frequency of 3 MHz have a penetration depth of about 2.9 cm, according to Formula 2, for soft tissue, such as muscle (here, 'a'-value for soft tissue was assumed as 1 dB cm$^{-1}$ MHz$^{-1}$ and b=1), whereas photons with a wavelength of about 720 nm and the highest optical penetration characteristics in biological tissue have a penetration depth of only 0.57 cm, according to Formula 1 (here $\mu_{eff}$=1.74 cm$^{-1}$ assumed). Here, the penetration depth was defined as the depth at which the exponential term at both falls to e$^{-1}$. However, it should be noted that, in Formula 1, the 1/r-term additionally exists. which makes the real penetration depth even lower.

Unlike conventional ultrasound imaging, in which an acoustic pulse is sent to the inside of a target object to be examined, first, and then a tomographic image of the object is produced by capturing the acoustic waves reflected from the object, PAI has to send a light pulse first; thus, as much light energy as possible has to be sent to the object in order to achieve large-depth imaging. Therefore, simply speaking, the imaging depth of a PAI system is mostly determined by how much energy can be delivered to the target object.

In this regard, it may be said that, in addition to the serious mismatch issue between an IA and an SA inside an object to be examined, existing array transducer-based PAE probes (Prior Documents 10 through 15) have such a light illumination structure that may not be able to achieve large-depth imaging. This is because the laser beams of those probes are emitted only through several specific points distributed around an array transducer; thus, the total amount of light energy that may be actually delivered to an object to be examined is very limited. When referring to the cases presented in Prior Documents 10 through 15, in which related PAE systems are actually implemented, the experimentally demonstrated imaging depth was limited to ~1 cm or less (in fact, the claimed imaging depth was not obtained from a real biological tissue; it came from an optical phantom). Indeed, the demonstrated imaging depth was much lower than the typical imaging depths of current array transducer-based EUS probes (Prior Documents 1) as well as those of the state-of-the-art PAI systems (typically known to be greater than 3 cm).

Of course, the above-described prior inventions may be able to further improve the imaging depth by simply increasing the amount of laser energy emitted through optical fibers (for example, as reported in Prior Document 15). However, in this case, those PAE systems may violate the safety limit regulations of the American National Standards Institute (ANSI) (see Prior Document 16), which state that the flow of light energy per unit area (1 cm$^2$) should not exceed 20 mJ, regardless of the flow direction anywhere on a surface of biological tissue during laser beam irradiation to the biological tissue.

In conclusion, most of the above-described inventions only focused on demonstrating the feasibility of a PAE system by using an array transducer; thus, their systems have fundamental limits in achieving an adequate probe size and large-depth imaging performance, which are required for GI endoscopy.

Therefore, taken together, the following important conclusions are reached.

In order to maximize the imaging depth of a PAE probe within a typical probe size allowed for GI endoscopy, although an ultrasonic transducer with a high sensitivity has to be employed, a light illumination unit (i.e., outlet) for an optical excitation of target tissue has to be designed to emit the related laser beam as uniformly as possible over the widest possible region. In fact, this is the most important technical point to be considered when designing such a PAE probe because, considering the safety limit (20 mJ/cm$^2$) and the maximally allowable size (1.3 cm×3 cm) of the distal section of a probe, the total amount of laser energy that may be actually delivered to an object to be examined is limited to about 78 mJ.

Since the maximum imaging depth of a PAI system is a dependent variable that is determined, to some extent, by the illumination dose, a given probe space has to be divided as effectively as possible for the illumination unit first, and other performance parameters, such as the sensitivity of an ultrasonic transducer, also have to be maximized. For reference, the steady-state optical fluence distribution ($\Phi$) formed inside a target object to be examined can be expressed approximately as a convolution of the spatial distribution $I(\vec{r}')$ of an incident beam onto the target surface and the Green's function $G(\vec{r}, \vec{r}')$, as shown in Formula 3, if the object is assumed as a semi-infinite homogenous medium (more exact formalism needs to reflect a boundary effect). And, it is known that the steady-state optical fluence distribution (i.e., Green's function) for a pencil beam incident to a target surface attenuates in a fashion similar to that seen in Formula 1. Thus, if the surface fluence does not exceed the safety limit, neither does the interior fluence.

$$\Phi(\vec{r}) = \int_S G(\vec{r}, \vec{r}')I(\vec{r}')ds' \qquad (3)$$

In summary, the key objective of the present disclosure is to provide a more advanced PAE probe structure that: 1) does not suffer from the mismatch issue between an IA and an SA that occurs in prior inventions and 2) enables large-depth imaging that approaches the theoretical limit of biomedical photoacoustics under the assumption of a typical probe size (~10-13 mm in diameter), allowed for clinical GI endoscopy, by using an array transducer as a signal detection mechanism and by adopting the general outer appearance and the typical size of conventional array transducer-based EUS probes as a morphological platform of the proposed PAE probe.

Additional aspects will be set forth in part in the description which follows and, in part, will be apparent from the description, or may be learned by practice of the presented embodiments.

According to an aspect of an embodiment, a photoacoustic-ultrasonic endoscope includes: an optical fiber; a light diffuser configured to diffuse a laser beam delivered through the optical fiber to a target point of an object to be examined; and an array transducer through which the diffused laser beam passes and configured to generate ultrasonic pulses or detect ultrasonic or photoacoustic waves generated in the object to be examined.

According to an aspect of another embodiment, a photoacoustic-ultrasonic endoscope includes: an optical fiber; a scanning head configured to diffuse a laser beam delivered through the optical fiber to a target point of an object to be examined; and an array transducer through which the diffused laser beam passes and configured to generate ultrasonic pulses or detect ultrasonic or photoacoustic waves generated in the object to be examined, wherein a light emitting area (LEA) where the diffused laser beam escapes from the scanning head and an ultrasonic sensor area (USA) of the array transducer overlap each other.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
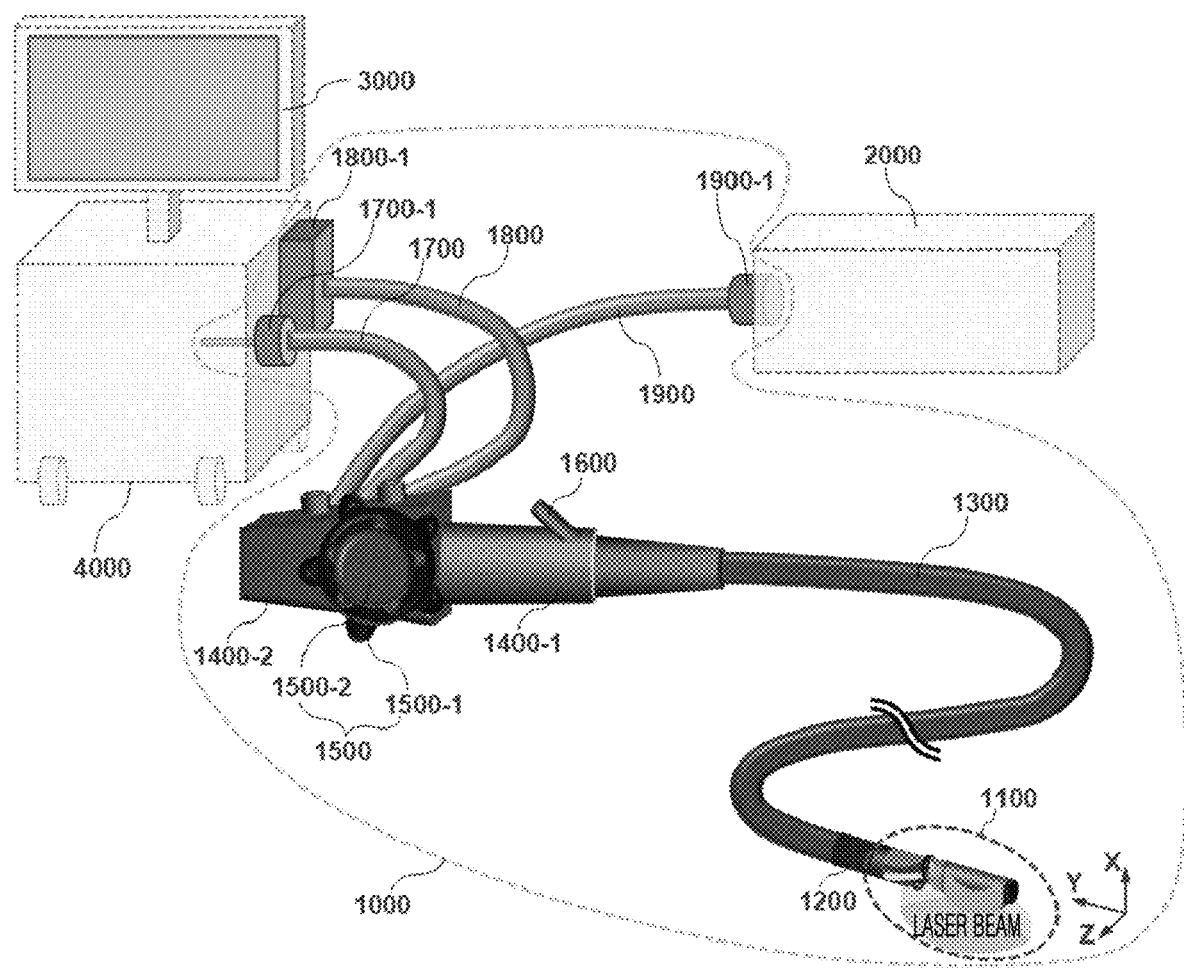
FIG. 1 is a view illustrating an overall configuration of an array transducer-based photoacoustic-ultrasonic endoscopic system according to an embodiment.

The present disclosure may include various embodiments and modifications, and embodiments thereof will be illustrated in the drawings and will be described herein in detail. The advantages and features of the present disclosure and methods of achieving the advantages and features will be described more fully with reference to the accompanying drawings, in which embodiments are shown. The present disclosure may, however, be embodied in many different forms and should not be construed as being limited to the embodiments set forth herein.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when an element is referred to as being "connected to" another element, it may be directly or indirectly connected to the other element. That is, for example, intervening elements may be present.

Expressions such as "at least one of", when preceding a list of elements, modify the entire list of elements and do not modify the individual elements of the list.

FIG. 1 is a view illustrating an overall configuration of an array transducer-based photoacoustic-ultrasonic (i.e., dual-mode) endoscopic system (hereinafter, also referred to as a PAE-EUS system) according to an embodiment. FIG. 1 illustrates a photoacoustic-ultrasonic endoscopic probe (hereinafter, the imaging probe is referred to as a PAE-EUS probe), peripheral systems for operating the PAE-EUS probe, and a connection relationship between the PAE-EUS probe and the peripheral systems.

Referring to FIG. 1, the PAE-EUS system according to an embodiment may include a PAE-EUS probe 1000 including a distal section 1100, an angulation section 1200, an insertion hose 1300, base grips 1400-1 and 1400-2, a direction control knob 1500, an accessory channel inlet 1600, a probe-console communication cable 1700, a transducer data cable 1800, and a guiding optical fiber cable 1900; a laser source 2000 that provides pulse-type light energy needed for photoacoustic imaging to the PAE-EUS probe 1000; and a system console 4000 that controls the PAE-EUS probe 1000, receives a detected photoacoustic signal and an ultrasonic signal from the PAE-EUS probe 1000, appropriately processes the photoacoustic signal and the ultrasonic signal, and displays the processed photoacoustic image and the ultrasonic image on a monitor 3000.

As described above, one of the objectives of the present disclosure is to provide a new configuration of the distal section 1100 that may solve the many limitations of existing array transducer-based PAE systems, e.g., insufficient probe miniaturization and poor imaging depth, by adopting the general shape and size of existing array transducer-based EUS probes utilized for GI endoscopy as a basic platform of the proposed device design.

Accordingly, due to this motivation, the general outer appearance of the PAE-EUS probe 1000 is similar to that of an existing array transducer-based EUS probe. However, the internal structure of the distal section 1100 is completely different from that of the existing array transducer-based EUS probe, and many elements, such as the guiding optical fiber cable 1900, which delivers a laser beam from the laser source 2000 to the PAE-EUS probe 1000, are added to the PAE-EUS probe 1000 to enable PAI. The function of each element will now be briefly explained with reference to FIG. 1.

The distal section 1100 is a key portion in which a light illumination unit and an ultrasonic detection unit are installed, and the distal section 1100 is inserted into an object to be examined during an actual endoscopic procedure to acquire a photoacoustic image or an ultrasonic image. First, the distal section 1100 may be implemented to have a diameter ranging from, but not limited to, about 1 cm to about 1.3 cm, in order to be applied to a GI endoscopy, as pursued by the present disclosure. The angulation section 1200 has a probe steering function, such as angulation or bending, so that the direction of the distal section 1100 can be effectively steered when the distal section 1100 approaches a target point along a narrow and curved path. That is, the angulation section 1200 can be bent along the X-Z plane that is perpendicular to the Y-axis that is coincident with the endoscopic hose axis, by manipulating the two direction control knobs 1500-1 and 1500-2 that are installed at the base of the PAE-EUS probe 1000. The insertion hose 1300, which is the main body of the PAE-EUS probe 1000, is physically flexible and has a slender and long hose-like shape; thus, it may allow the distal section 1100 to be effectively inserted into the target point, which might only be accessible through a narrow and curved path. The insertion hose 1300 may have a diameter ranging from about 1 cm to about 1.3 cm, which is similar to that of the distal section 1100, and a length ranging from about 0.8 m to about 2 m. The outer surface of the insertion hose 1300 may be coated with a thin layer of a soft and flexible polymer, as is the case with an existing clinical video endoscope. A number of electric wires and optical fibers pass through the inside of the insertion hose 1300, and additional channels may also be formed.

The base grips 1400-1 and 1400-2 that allow a clinician to hold and manipulate the PAE-EUS probe 1000 easily may be connected to a base part of the insertion hose 1300, and the accessory channel inlet 1600, through which an accessory instrument may be inserted, protrudes obliquely from a side of the base grip 1400-1. The accessory channel inlet 1600 may have an internal diameter ranging from about 2.7 mm to about 3.8 mm in general, and thus a variety of accessory instruments may be introduced into the accessory channel inlet 1600. An inserted accessory instrument may pass through the insertion hose 1300 and be projected from an accessory channel outlet 1170 (see FIG. 2) installed at the distal section 1100.

Three different types of cables may be connected to one side of the base grips 1400-1 and 1400-2 (e.g., 1400-2, as shown in FIG. 1). One cable is the guiding optical fiber cable 1900 in which an optical fiber or optical fiber bundle for delivering a laser beam emitted from the laser source 2000 to the base grip 1400 is embedded. The guiding optical fiber cable 1900 may be connected to the laser source 2000 via a guiding optical fiber cable adapter 1900-1, and the opposite end of the guiding optical fiber cable 1900 may be connected to the optical fiber 1113 (see FIG. 2) that is located inside the insertion hose 1300 (see FIG. 2). Alternatively, the guiding optical fiber cable 1900 may be a part (i.e., a physical extension) of the optical fiber 1113. Another cable is the probe-console communication cable 1700 that includes a number of electric wires configured to control the overall operational process of the PAE-EUS probe 1000 and transmit a video image provided by an ultra-small charge-coupled device (CCD) camera 1150 mounted in the distal section 1100. The probe-console communication cable 1700 is connected to the system console 4000 via a probe-console communication cable adapter 1700-1. The last cable is the transducer data cable 1800 that transmits a photoacoustic signal and an ultrasonic signal detected by the array transducer 1111, which will be explained later. The transducer data cable 1800 may also transmit a series of electric pulses to the array transducer 1111 when an ultrasound imaging mode is initiated. The transducer data cable 1800 is also connected to the system console 4000 via a transducer data cable adapter 1800-1.

The configurations and functions of several major parts of the PAE-EUS probe 1000 and its peripheral systems have been briefly explained. For reference, the system composition and configuration shown in FIG. 1 is only an example provided for better understanding; some other subsidiary elements may be added and, if necessary, the laser source 2000 and the system console 4000 may be integrated as a single unit. In this case, the probe-console communication cable 1700, the transducer data cable 1800, and the guiding optical fiber cable 1900 have to be appropriately modified, and they may be integrated into a single cable.

Figure 2:
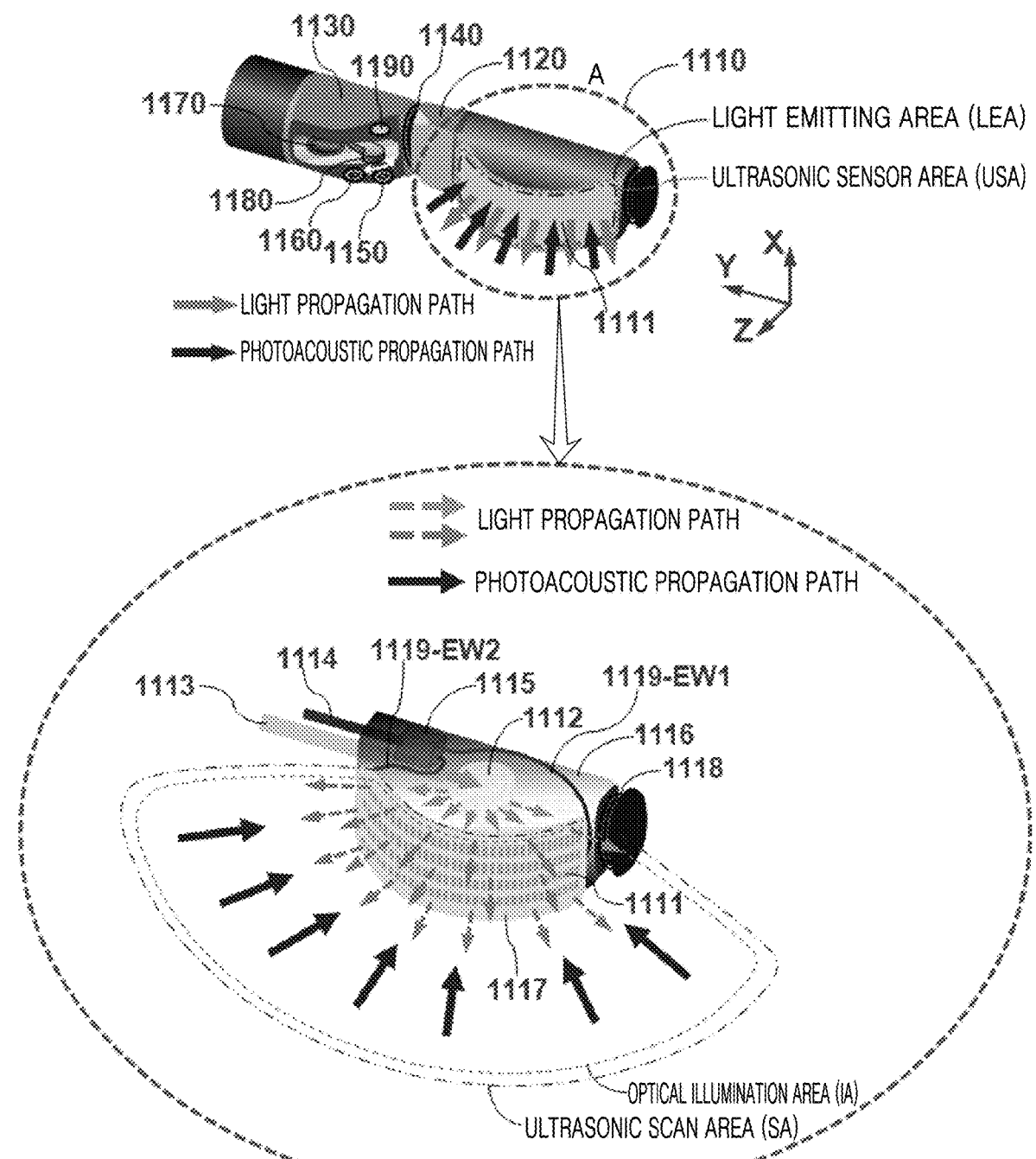
FIG. 2 is a view illustrating an outer appearance of the distal section of an endoscopic probe and a perspective view of the interior of region A.

As mentioned above, one of the main objectives of the present disclosure is to provide a more advanced scanning head structure that can achieve an imaging depth that is much better than those of existing PAE systems, while maintaining a conventional image scanning (or image presentation) style, such as a two-dimensional (2D) planar sector or a three-dimensional (3D) volumetric sectoral image, and the general outer appearance and size of an array transducer-based side-scanning EUS probe that is currently utilized in clinics. FIG. 2 shows one of the embodiments derived to achieve this objective; it illustrates the structure of an embodiment of the distal section 1100, including a scanning head 1110 and other major elements distributed around the scanning head 1110, and a magnified 3D perspective view (i.e., the bottom image enclosed by a dashed circle) showing the interior of region A, which shows how the light illumination unit and the ultrasonic detection unit are configured inside the scanning head 1110.

To be more specific, the present disclosure has worked out an internal structure of the scanning head 1110, which includes a light diffuser 1112 and an optically-transparent array transducer 1111 as core elements, in order to maximize the imaging depth according to the general principle of PAI within the available size of about 1.3 cm×3 cm and the outer appearance of a scanning head, as shown in FIG. 2; the dashed bottom image in FIG. 2 is a perspective view representing a general concept for the region corresponding to A in the upper image. Here, at least a portion of the array transducer 1111 may be formed to be optically-transparent (but, the transparency does not always mean a perfect transparency).

The main elements of the distal section 1100, shown in FIG. 2, and their basic functions will now be explained.

As mentioned, FIG. 2 illustrates the distal section 1100, which is an end portion of the entire PAE-EUS probe 1000 shown in FIG. 1; the distal section 1100 is connected to the angulation section 1200, and it includes the scanning head 1110. First, the scanning head 1110 is the key portion to which a core concept of the present disclosure is applied, and when a PAI mode is initiated, the scanning head 1110 approaches a target point to be examined, emits a laser beam, and detects a generated photoacoustic signal. The scanning head 1110 may be firmly fixed by the scanning head base frame 1120, which bridges the scanning head 1110 and the hose end frame 1130, and, on the distal end of the scanning head 1110, a first groove for balloon fixation 1118 may be formed. The first groove for balloon fixation 1118 may be a ring-shape groove, and it can be used for mounting an acoustic matching balloon, which might be needed for an actual endoscopic procedure, along with the second groove for balloon fixation 1140, which is formed between the hose end frame 1130 and the scanning head base frame 1120. A detailed method for using the first/second groove for balloon fixation 1118/1140 will be explained later.

An ultra-small CCD camera 1150 may be installed on an inclined side of the hose end frame 1130 in order to provide real-time video images; this enables the PAE-EUS probe 1000 to more effectively approach a target point to be examined during an actual clinical procedure. Moreover, a visual-field illumination unit 1160 that provides light with a predetermined color may be installed next to the ultra-small CCD camera 1150 so that the ultra-small CCD camera 1150 could clearly image objects even in a dark condition.

A hole, similar to a coin slot, may also be formed in the inclined side of the hose end frame 1130 so that the accessory channel outlet 1170 and a biopsy needle lever 1180 can be installed inside the hole. The biopsy needle lever 1180, which can be installed next to the accessory channel outlet 1170, could be utilized to adjust the direction of a biopsy needle (not shown) projected from the accessory channel outlet 1170 so that fine needle aspiration (FNA), or a similar procedure, could be effectively performed based on the combined photoacoustic-ultrasonic dual-mode image provided by the present endoscopic system. The mentioned biopsy needle (not shown) may be inserted into the accessory channel inlet 1600, shown in FIG. 1, advanced forward along a predetermined channel (i.e., the accessory channel) formed inside the insertion hose 1300, and then ejected from the predetermined channel via the accessory channel outlet 1170 shown in FIG. 2.

In addition, a waterjet nozzle 1190, for washing out the unwanted materials attached to a surface of the ultra-small CCD camera 1150 or the like, at any time during the process of inserting the scanning head 1110 of the PAE-EUS probe 1000 into the object to be examined, may be installed on an edge of the inclined side of the hose end frame 1130.

While the main elements of the distal section 1100 have been explained, the elements shown in FIG. 2 are only several of the possible examples that may be needed to effectively realize the main concept derived by the present disclosure; thus, some other system elements, obviously required by common sense, may be added, elements that are not necessarily required may be excluded, and the positions of the aforementioned elements may also be appropriately changed, depending on the application direction. For example, the hose end frame 1130 and the scanning head base frame 1120 may be formed as a single piece instead of as separate pieces, the positions of the visual-field illumination unit 1160 and the ultra-small CCD camera 1150 may be changed, and the number of visual-field illumination units 1160 and ultra-small CCD cameras 1150 may also be increased.

The features of the scanning head 1110 will now be explained with reference to the perspective view (i.e., the lower image) of FIG. 2, which is magnified from region A.

According to the present disclosure, a PAE-EUS probe includes the optical fiber 1113, the scanning head 1110, configured to diffuse and send a laser beam delivered through the optical fiber 1113 to a target point to be examined, and the array transducer 1111, through which the diffused laser beam may pass and be configured to generate ultrasonic pulses or detect the ultrasonic or photoacoustic waves propagating from the target point. Thus, the light emitting area (LEA), through which the diffused laser beam is emitted from the scanning head 1110, and the ultrasonic sensor area (USA), where multiple ultrasonic sensor elements are distributed constituting the array transducer 1111, overlap each other.

Referring to FIG. 2, the laser beam that passes through the array transducer 1111 is emitted from the scanning head 1110 and sent to an object (not shown) to be examined.

That is, the core concept of the present disclosure is that, unlike the prior inventions, the LEA, through which a laser beam is emitted, and the USA, where the multiple ultrasonic sensor elements are distributed, overlap each other instead of being arranged separately. Consequently, the aforementioned mismatch issue between an optical IA and an ultrasonic SA and the limited illumination energy issue of the prior inventions can be solved.

The PAE-EUS probe, including the light diffuser 1112 and the array transducer 1111, which share a common aperture to maximize the span areas of the LEA and the USA within the available size (which may be about 1.3 cm×3 cm) of the scanning head 1110, will now be explained.

The PAE-EUS probe according to an embodiment includes the optical fiber 1113, the light diffuser 1112, configured to diffuse a laser beam delivered through the optical fiber 1113 to a target point to be examined, and the array transducer 1111, through which the diffused laser beam may pass and be configured to generate ultrasonic pulses or detect the ultrasonic or the photoacoustic waves propagating from the object.

Referring to the perspective view presented in FIG. 2 (i.e., the lower image), it can be seen that one or multiple strands of optical fiber 1113 are placed inside the insertion hose 1300 and extend to the distal section 1100 of the PAE-EUS probe 1000. Consequently, a laser beam that is delivered through the optical fiber 1113 is diffused and expanded over the entire area where the array transducer 1111 is distributed by the light diffuser 1112 located at the central region of a scanning head casing 1116; the laser beam then passes through the array transducer 1111 and is finally sent to the target object.

Once the laser beam penetrates into a surface of the object, it is rapidly diffused and absorbed by the object, thereby generating photoacoustic waves. Afterwards, some of the generated photoacoustic waves propagate to the array transducer 1111, where they are detected and finally converted into an electrical signal according to the piezoelectric effect of the array transducer 1111. That is, the array transducer 1111 drawn by the present disclosure is a component that can detect the generated photoacoustic waves based on the piezoelectric effect, and the array transducer 1111 also can send ultrasonic pulses to the object when an ultrasonic imaging mode is initiated, like conventional PAI systems. However, the main feature that differentiates the present endoscope from the prior PAE systems is that the light energy required for the photoacoustic excitation of target tissue can be more effectively spread over the entire SA of the array transducer 1111; thus, photoacoustic waves with a more uniform spatial distribution can be induced. That is, the laser beam diffused by the light diffuser 1112 can be more effectively delivered to the target object through the entire span area of the array transducer 1111 (i.e., USA). For reference, an approximate intensity distribution of photons inside a target tissue when a laser beam penetrates into the target tissue can be calculated based on Formula 1 and Formula 3.

After the photoacoustic waves are converted into electrical signals by the multiple piezoelectric elements constituting the array transducer 1111, the signals are sent to a first hub 1115 via the local electric wire bundles 1119-EW1 and 1119-EW2; the signals are then, finally, delivered to the system console 4000 further passing through the electric wire bundle 1114 installed inside the insertion hose 1300 of the PAE-EUS probe 1000. That is, the electric wire bundle 1114 originating from the scanning head 1110 may extend to the transducer data cable adapter 1800-1, shown in FIG. 1, as a continuous unit. Here, the first hub 1115 may function as a junction or connection point that electrically connects the local electric wire bundles 1119-EW1 and 1119-EW2 in the scanning head 1110 and the electric wire bundle 1114 in the insertion hose 1300. However, if necessary, the first hub 1115 may also include other functions, such as pre-amplification and multiplexing.

Since the PAE-EUS system, according to the present disclosure, includes the array transducer 1111 as an ultrasound detector, the PAE-EUS system can provide not only a photoacoustic image but also a conventional ultrasound image. Thus, if an ultrasound imaging mode is initiated, a series of electrical pulses, which are set to have specific phases that are different from one another according to a predetermined purpose, are generated from the system console 4000 and sent to the individual piezoelectric elements of the array transducer 1111 to generate ultrasonic pulses, after sequentially passing through the transducer data cable 1800 and the insertion hose 1300. Then, the generated ultrasound pulses propagate toward the object, and a portion of the ultrasound pulses are bounced back from the object and detected by the array transducer 1111; they are then further delivered to the system console 4000 in reverse order of the explained pulsing process, and finally displayed as an image on the monitor 3000.

Such photoacoustic-ultrasonic dual-mode imaging sequences may occur very quickly and alternately at a predetermined time interval, as described in Prior Document 17, and pieces of the data obtained according to the photoacoustic-ultrasonic imaging sequence may be processed once a predetermined amount of data set is obtained, and this may be simultaneously displayed on the monitor 3000.

In conclusion, the array transducer 1111, according to the present disclosure, must have the capability of transmitting a laser beam very effectively therethrough as well as the conventional ultrasound pulsing and detecting function. Several possible embodiment methods will be explained later.

The PAE-EUS probe according to an embodiment may further include an acoustic matching layer 1117 that covers at least a portion of the outer surface of the array transducer 1111 and made of a material through which light can be transmitted. For example, acoustic matching layer 1117 may cover the entire outer surface of the array transducer 1111.

Referring to the perspective view presented in FIG. 2 (i.e., the lower image), a surface of the array transducer 1111 may be covered with the acoustic matching layer 1117 made of a polymer-based material in order to protect the surface of the array transducer 1111 and provide an adequate acoustic matching condition between the array transducer 1111 and an object or ambient immersion medium. Consequently, the acoustic matching layer 1117 also needs to be optically transparent; it may be preferable that the acoustic matching layer 1117 be made of a polymethylpentene (TPX)-based material due to the required acoustic and optical characteristics. TPX is a material that permits light to be very easily transmitted therethrough, and it also has low acoustic impedance close to that of the general soft tissues of humans.

According to an embodiment, the LEA, through which a diffused laser beam is emitted from the array transducer 1111, and the USA, where the array transducer 1111 is distributed, may overlap each other.

The LEA refers to a surface from which light or a laser beam is emitted among the entire outer surface of the array transducer 1111. The LEA may overlap the USA where the array transducer 1111 is distributed. That is, the outer surface or the inner surface of the array transducer 1111 is both the LEA and the USA. Due to this arrangement, the mismatch issue between an IA and a SA and the deliverable energy limit issue of prior inventions are solved.

In general, in an array transducer-based PAE probe, an electric wire bundle including multiple signal wires has to pass through the insertion hose of the PAE probe, as it does in a conventional EUS probe; this means that the final space allowed for the installation of an optical fiber is very limited. Hence, considering the general thickness (i.e., ~10-13 mm in diameter) of the insertion hose of a clinical EUS probe, the maximally allowable size for the installation of the optical fiber might only be about 5 mm in diameter, which eventually makes the optical fluence at the outlet of the optical fiber very high. Moreover, due to the numerical aperture (NA) of the optical fiber, the laser beam emitted through the optical fiber shows a diverging behavior in proportion to the NA; that is, the individual photons emitted from the optical fiber may propagate in irregular directions rather than being collimated.

Under the explained system condition, and many other system requirements, in order to effectively guide a laser beam emitted through the optical fiber 1113 to a position where the array transducer 1111 is located with minimal or no loss, and also to uniformly spread the laser beam over an entire area where the array transducer 1111 is distributed, a PAE-EUS probe, according to an embodiment of the present disclosure, includes a light diffuser 1112 or a scattering light diffuser 1112OD (see FIG. 3) with predetermined optically diffusive or scattering properties.

Basically, the light diffuser 1112 may be a combined module of a lens or a mirror, a diffuser, or other optical elements. Hereinafter, several embodiments of the light diffuser 1112 will be explained in detail with reference to FIGS. 3 through 5.

Figure 3:
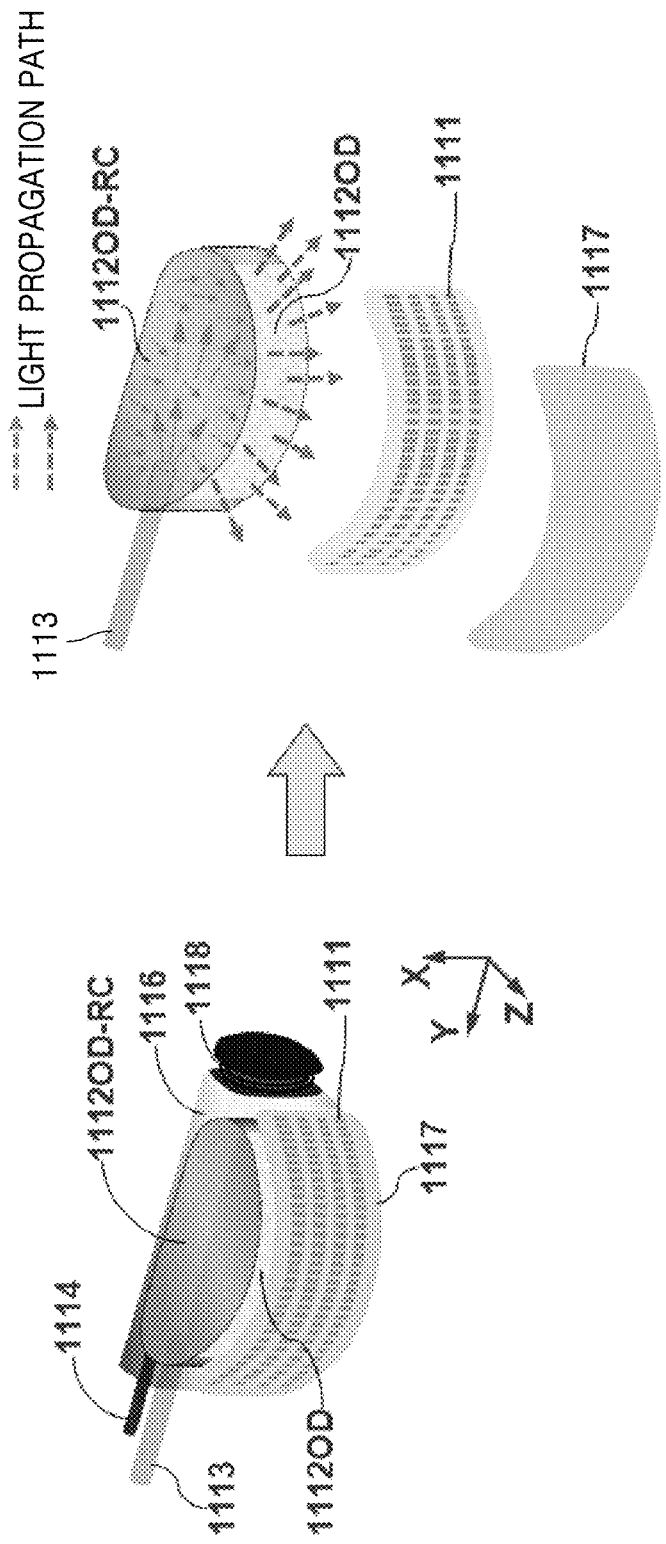
FIG. 3 is a view of a light diffuser and a perspective view illustrating elements of the light diffuser according to an embodiment.

FIG. 3 is a view of the light diffuser 1112 and a perspective view illustrating the elements of the light diffuser 1112 according to an embodiment.

According to an embodiment, the light diffuser 1112 may include a portion that is convex outward. The scattering light diffuser 1112OD that will be explained below may be an example of the light diffuser 1112.

Referring to FIG. 3, the light diffuser 1112 or the scattering light diffuser 1112OD may have a D-shape block structure whose one side is convex, and it may be located behind the array transducer 1111 (along the −Z direction) and at the central region of the scanning head casing 1116.

According to an embodiment, at least a portion of the outer surface of the scattering light diffuser 1112OD may include an internal reflection coating layer 1112OD-RC that sends such a light, which propagates from the inside of the scattering light diffuser 1112OD toward the outside of the scattering light diffuser 1112OD after experiencing multiple scattering events therein, back into the scattering light diffuser 1112OD.

The light diffuser 1112 or the scattering light diffuser 1112OD may be formed so that all the surfaces, other than the surface that directly contacts the array transducer 1111 and the optical fiber 1113, are coated with a material with high internal light reflection characteristics, in addition to the mentioned light diffusion characteristics. This is because, among all the photons that are spatially homogenized by the scattering light diffuser 1112OD, any photons that are about to leave the scattering light diffuser 1112OD through the unwanted surface that is not closely adjacent to the LEA need to be sent back to the central region of the scattering light diffuser 1112OD, as much as possible, in order to increase the total amount of light energy emitted from the array transducer 1111 to a target object (refer to the light propagation path shown in the right perspective view of FIG. 3). In the present disclosure, this light reflection layer is referred to as the internal reflection coating layer 1112OD-RC and, due to its contribution, the total number of photons emitted from the array transducer 1111 is significantly increased.

That is, in the present disclosure, the scattering light diffuser 1112OD, including the internal reflection coating layer 1112OD-RC, may be another important system element. However, in order to derive a more effective performance for the scattering light diffuser 1112OD, a base (substrate) material needs to be designed to have more appropriate optical properties. Here, the optical properties refer to parameters, such as an absorption coefficient $\mu_a$, a scattering coefficient $\mu_s$, and an anisotropy factor g, which are typically utilized for modeling a light propagation phenomenon in biological tissue according to the theory of tissue optics.

According to an embodiment, a reduced scattering coefficient $\mu_s'$ of the light diffuser 1112 may be equal to or greater than 0.1 cm$^{-1}$ and equal to or less than 1.0 cm$^{-1}$. That is, for example, a reduced scattering efficient of the scattering light diffuser 1112OD may be about 0.67 cm$^{-1}$. A reduced scattering coefficient ($\mu_s'$) is a parameter that has a relationship $\mu_s'=\mu_s(1-g)$ with a scattering coefficient ($\mu_s$) and an anisotropy coefficient (g). If we assume a reduced scattering coefficient value of 4 cm$^{-1}$, for example, this means that whenever a photon travels every 0.25 cm (=¼ cm$^{-1}$), the photon would be scattered in all directions (i.e., omnidirectionally) with the same probability. In the present disclosure, the reason why the reduced scattering coefficient value of ~0.67 cm$^{-1}$ is suggested is that the scanning head 1110 may be formed within a space with a diameter of ~1.3 cm and a length of ~3 cm. In this case, most of the photons emitted from the optical fiber 1113 would travel ~1.5 cm, which is half of the total length (3 cm) of the scanning head 1110, without experiencing any scattering event, and then they would be scattered in all directions with the same probability. This is because the dimension, 1.5 cm, corresponds to the transport mean free path ($l_t'\equiv 1/\mu_t'\approx 1/\mu_s'$) of the scattering light diffuser 1112OD.

According to an embodiment, the light diffuser 1112 may be formed with a plastic resin, such as polypropylene, or ground glass, or an engineered diffuser. Although, in reality, the absorption coefficient ($\mu_a$) value of the light diffuser 1112 or the scattering light diffuser 1112OD may not be perfectly zero (0), it is preferable that the absorption coefficient ($\mu_a$) has a value as low as possible because the scattering light diffuser 1112OD may also absorb light by itself, and it may convert the absorbed light energy into heat. For example, since polypropylene has a very low light absorption coefficient and a reduced scattering coefficient value (typically about 0.6 cm$^{-1}$ at a wavelength of 650 nm), polypropylene, or other materials in its family, may be a possible substrate material that satisfies the aforementioned requirements.

Based on the size (e.g., a diameter of 1.3 cm and a length of 3 cm) of the scanning head 1110 and the reduced scattering coefficient, the energy flow or spatial distribution of the photons may be predicted as follows. First, most of the photons emitted from the optical fiber 1113 may proceed toward the central region of the scanning head 1110 without being greatly deflected from their initial emitted directions, and then they would be almost uniformly scattered in all directions near the center. Among those photons, the photons scattered toward the array transducer 1111 may be able to reach the surface of an object to be examined without experiencing much difficulty as they travel, after sequentially passing through the array transducer 1111 and the acoustic matching layer 1117, although there could be some more additional scattering events as they travel. However, the photons scattered toward the opposite direction of the array transducer 1111's location, which might also experience some more additional scattering events as they travel, eventually can be sent back to the array transducer 1111 by the internal reflection coating layer 1112OD-RC. Consequently, the final photon flux delivered to the target object could be greatly augmented by the explained process.

According to an embodiment, the optical fiber 1113 may be inserted into the light diffuser 1112.

Referring to the right perspective view presented in FIG. 3, an end portion of the optical fiber 1113 may be slightly inserted into the scattering light diffuser 1112OD. According to this structure, the photons emitted from the optical fiber 1113 may be more effectively guided (with a higher probability) to the central region of the scattering light diffuser 1112OD. This is because, if an end of the optical fiber 1113 directly contacts a surface of the scattering light diffuser 1112OD, unlike the configuration shown in FIG. 3, many portions of the photons emitted from the optical fiber 1113 could bounce back from the surface of the scattering light diffuser 1112OD and then get sent back to the optical fiber 1113 again.

Figure 4:
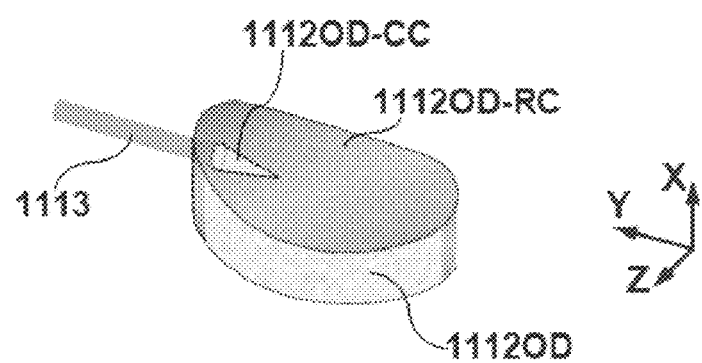
FIG. 4 is a view illustrating a shape of the light diffuser according to an embodiment.

FIG. 4 is a view illustrating a shape of the light diffuser 1112 according to an embodiment.

According to an embodiment, the light diffuser 1112 may have an empty space, and an end point of the optical fiber 1113 may be located inside the empty space.

Referring to FIG. 4, a cavity 1112OD-CC with a conical shape is formed over an interval along the direction extending from the end portion of the optical fiber 1113 to the central region of the scattering light diffuser 1112OD. According to this structure, excessive back-scattering events of photons, which may occur right in front of the outlet of the optical fiber 1113, can be greatly reduced. However, in forming the cavity 1112OD-CC, its shape does not need to be conical; other adequate variations are possible. Moreover, the distal shape of the optical fiber 1113 may be altered to have any other optimal structure depending on the shape of the cavity that is redesigned.

Figure 5:
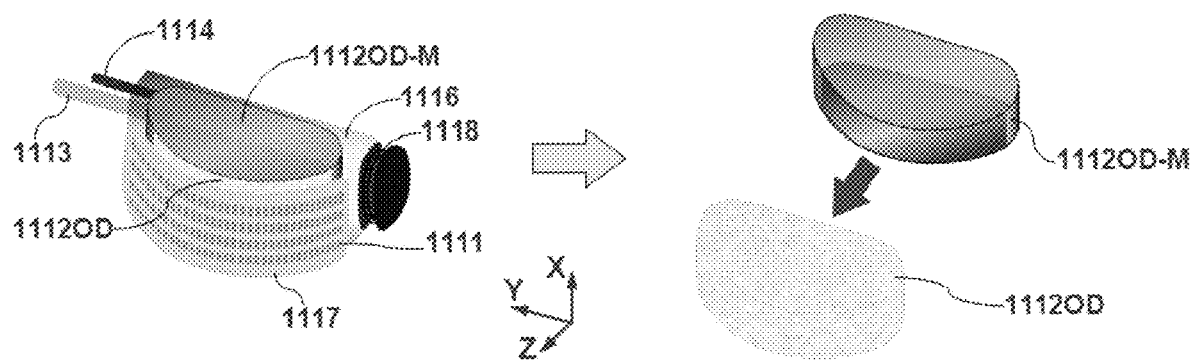
FIG. 5 is a view of the light diffuser and a perspective view illustrating elements of the light diffuser according to another embodiment.

FIG. 5 is a view of the light diffuser 1112 and a perspective view illustrating the elements of the light diffuser 1112 according to another embodiment.

The PAE-EUS probe according to an embodiment may further include a light reflection mirror 1112OD-M that surrounds an outer surface of the scattering light diffuser 1112OD and has at least a portion that is open in order to emit the laser beam diffused by the scattering light diffuser 1112OD to outside.

Referring to the right perspective view presented in FIG. 5, the light reflection mirror 1112OD-M that surrounds the scattering light diffuser 1112OD may be located outside the scattering light diffuser 1112OD. The light reflection mirror 1112OD-M may be formed in the shape of a baseball glove-like 3D structure, which has a surface contour like a 'D'-block (i.e., it is very similar to the outer surface contour of the scattering light diffuser 1112OD), but whose one side is open along the convex, outward surface thereof. That is, the inner space of the light reflection mirror 1112OD-M is empty and the reflective surface for light reflection is formed on an inner surface of the light reflection mirror 1112OD-M, but at least a portion of the light reflection mirror 1112OD-M is open in order to emit the laser beam diffused by the light diffuser 1112 to the array transducer 1111. Consequently, although the photons emitted from the optical fiber 1113 are diffused omni-directionally after passing through the light diffuser 1112, most of the photons can be effectively guided to the convex surface of the light diffuser 1112, which abuts the array transducer 1111, by the light reflection mirror 1112OD-M, and finally be delivered to a target tissue after passing through the array transducer 1111.

As described above, the scattering light diffuser 1112OD guides the laser beam emitted from the optical fiber 1113 to the array transducer 1111 with minimal energy loss, while also creating an optical intensity distribution as uniform as possible over the array transducer 1111's span area. However, in addition to the mentioned light-diffusing function, the scattering light diffuser 11112OD may also function as a sound absorber that scatters and absorbs any unwanted sound waves propagating from the array transducer 1111, i.e., acoustic reverberations that could potentially generate artifacts in an obtained image. Moreover, the shape of the scattering light diffuser 1112OD is not limited to the 'D'-block shape; its shape may be altered to other forms depending on the application area. For example, the scattering light diffuser 1112OD may be formed like a thick circular disc (i.e., not a 'D'-block shape), or a curved thin film when it is necessary to locate it right behind (along the −Z direction) the array transducer 1111 as a film.

The key concept of the present disclosure is to maximize both an LEA and a USA by arranging them to overlap each other; this overlap can be realized if an array transducer with optical transparency is employed. Hereinafter, the detailed structures of several possible embodiments of such an array transducer 1111 are explained.

According to an embodiment, the array transducer 1111 that is optically transparent may comprise a piezoelectric layer with a predetermined thickness, a group of first electrodes arranged on one surface of the piezoelectric layer in a one-dimensional (1D) or 2D fashion, and another group of second electrodes arranged on the other surface of the piezoelectric layer in parallel to the first electrodes. In this embodiment, possible examples of a piezoelectric material that can be utilized for the piezoelectric layer may include a polymer, ceramics, and a single crystal, and, in the array transducer 1111, the piezoelectric layer may be formed as a continuous single piece or multiple pieces.

Figure 6:
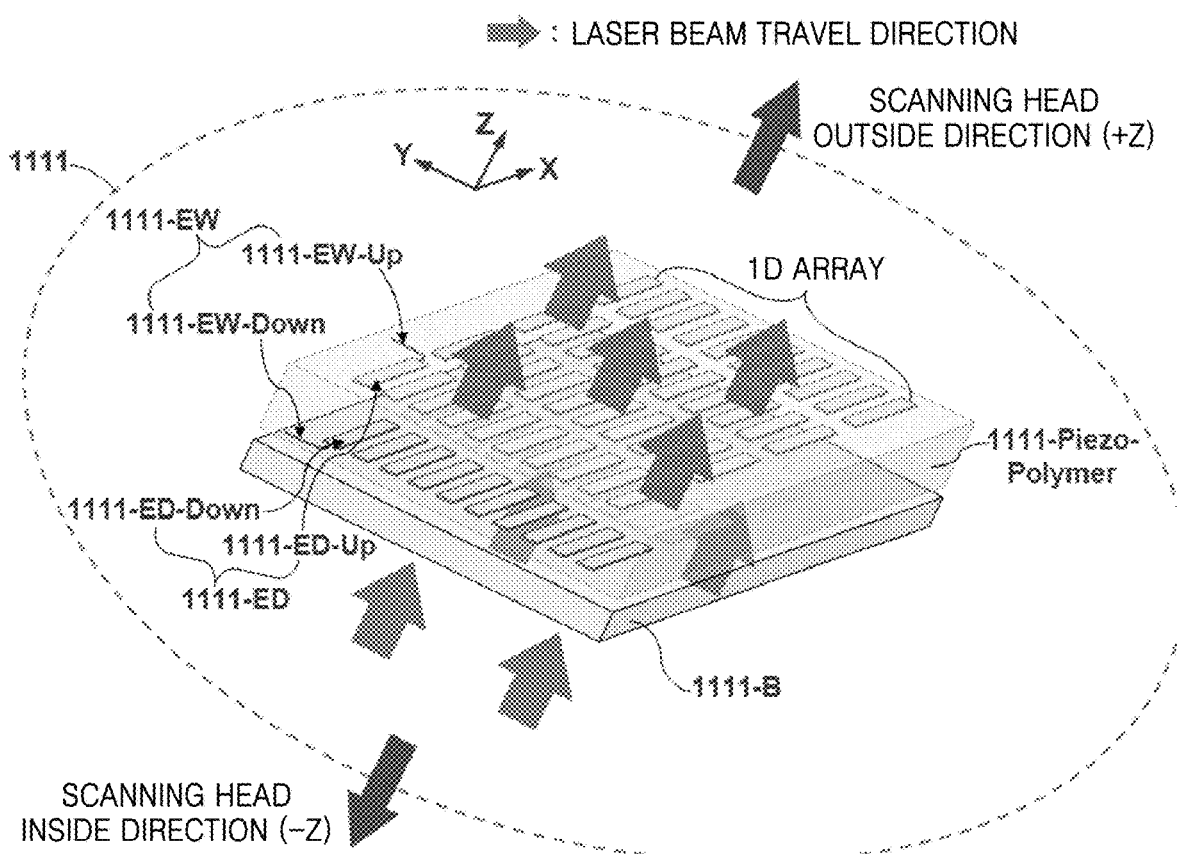
FIG. 6 is a view illustrating the structure of a portion of an array transducer implemented using a piezoelectric polymer film and transparent electrodes.

FIG. 6 is a view illustrating the structure of a portion of the array transducer 1111 implemented using a piezoelectric polymer film and transparent electrodes.

As seen in FIG. 6, a piezoelectric polymer film 1111-Piezo-Polymer is located between the first electrodes 1111-ED-Up and the second electrodes 1111-ED-Down. That is, FIG. 6 illustrates a case in which the piezoelectric layer is made of a piezoelectric polymer film 1111-Piezo-Polymer. In this case, it is preferable that the polymer-based piezoelectric material has such an optical property that light waves can easily pass through it. Thus, possible examples of the piezoelectric material that satisfy this condition may include polyvinylidene fluoride (PVDF) and poly[(vinylidenefluoride-co-trifluoroethylene)] P(VDF-TrFE), which is a copolymer of PVDF.

It is well known that, since a polymer-based piezoelectric material has a lower electromechanical coupling coefficient (k) than that of a ceramic-based piezoelectric material, the polymer-based piezoelectric material has relatively low energy efficiency. Here, the electromechanical coupling coefficient (k) refers to the conversion efficiency of mechanical energy to electric energy. Thus, for example, if the k-value of a piezoelectric material is low, the maximum signal sensing depth of the related ultrasonic senor is also low for a given unit electrical energy input. However, the polymer-based piezoelectric material exhibits very high electrode-voltage response characteristics for a unit physical deformation because the total electric charges induced by a unit deformation at an electrode are relatively low due to its low dielectric permittivity ($\epsilon$). Thus, if a pre-amplifier with an adequate electrical input impedance matching the output impedance of the polymer-based piezoelectric sensor is employed, signal sensitivity comparable to that of a ceramic sensor could be achieved.

Leaving aside the mentioned advantage, since the key objective of the present disclosure is to provide an advanced PAE-EUS probe structure with a more enhanced PAI capability rather than an ultrasound imaging capability, such a low electromechanical coupling coefficient of a piezoelectric polymer film may not be a big issue. This is true because, unlike conventional ultrasound imaging, which requires two electromechanical conversion processes, including the ultrasonic pulse emission to an object to be examined through the first electro-mechanical conversion and the detection of reflected acoustic waves after a predetermined time interval through the second mechano-electrical conversion, PAI only requires one mechano-electrical conversion process. That is, since only one mechano-electrical conversion process is involved in PAI, and also the maximum imaging depth of a PAI system is mainly determined by the optical illumination parameters, as described above, the relatively low electromechanical coupling coefficient value of a polymer-based piezoelectric material is not a big concern.

In addition to the electrical characteristics, a polymer-based piezoelectric sensor has other advantages; it is inexpensive, it is flexible, and its sub-elements, such as electrodes or electric wires, may be easily formed in a desired pattern on its surface.

Referring back to FIG. 6, the array transducer 1111 may include a number of first electrodes 1111-ED-Up and second electrodes 1111-ED-Down, which are formed on both surfaces of the piezoelectric polymer film 1111-Piezo-Polymer with a predetermined thickness. That is, the piezoelectric polymer film 1111-Piezo-Polymer acts as a kind of a wafer, and the first electrodes 1111-ED-Up and the second electrodes 1111-ED-Down are formed in parallel so that each pair can function as one unit of ultrasonic sensor element.

Here, the electrodes 1111-ED, including a number of first electrodes 1111-ED-Up and second electrodes 1111-ED-Down, may be arranged in a 1D linear or 2D planar pattern. That is, multiple pairs of electrodes 1111-ED formed on both surfaces of the piezoelectric polymer film 1111-Piezo-Polymer, like a parallel-plate, may be arranged along the Y-axis to form a 1D array, and, if necessary, additional groups of 1D arrays may be expanded along the X-axis to form a 2D array. In this case, since the center frequency ($f_c$) of the array transducer 1111 is mostly determined by the thickness of the piezoelectric polymer film 1111-Piezo-Polymer, and because the sound receiving angle of each element, through which an ultrasonic beam approaches the element, and the sensitivity of each element are mostly determined by X- and Y-axis widths of electrodes, the thickness of the piezoelectric polymer film 1111-Piezo-Polymer and the X and Y-widths of the electrodes have to be carefully determined, depending on the acoustic performance desired.

According to an embodiment, the first electrodes 1111-ED-Up and the second electrodes 1111-ED-Down may be optically transparent.

If the electrodes 1111-ED formed on both surfaces of the piezoelectric polymer film 1111-Piezo-Polymer are made of an optically-transparent material, as mentioned above, the laser beam approaching from the light diffuser 1112 can pass through the electrodes 1111-ED without energy loss; thus, the LEA can also be maximized within the limited size of the scanning head 1110. In this case, the electric wires 1111-EW, which deliver the input/output current to/from the electrodes 1111-ED, must also be optically transparent; to satisfy these requirements, the electrodes 1111-ED and the electric wires 1111-EW can be made of any of the following materials or related material groups: indium tin oxide (ITO), indium zinc oxide (IZO), zinc oxide (ZnO), indium oxide ($In_2O_3$), Ge-doped $In_2O_3$ (IGO), and aluminum-doped zinc oxide (AZO), or any other materials with the mentioned characteristics.

That is, since the electric wires 1111-EW, the electrodes 1111-ED, and the piezoelectric polymer film 1111-Piezo-Polymer included in the array transducer 1111 are all optically transparent, the laser beam diffused by the light diffuser 1112 can be delivered to the object to be examined over the entire area where the array transducer 1111 spans.

The PAE-EUS system according to an embodiment may further include a sub-unit of the system console 4000 or a related function that processes a set of detected photoacoustic and ultrasonic signals to produce a PAE-EUS image and also remove the image artifacts that occurred due to the photoacoustic waves generated by the first electrodes 1111-ED-Up and the second electrodes 1111-ED-Down.

Although the first electrodes 1111-ED-Up and the second electrodes 1111-ED-Down are optically transparent, their absorption coefficients may not be perfectly zero (0), in reality; thus, they may absorb some amount of the laser energy, which resultantly generates unwanted photoacoustic waves. The unwanted photoacoustic waves may be mixed with the normal photoacoustic waves generated in the object to be examined at the same moment; thus, they may be detected together as a signal, and may appear as an artifact in an obtained image.

If the mentioned image artifacts are not negligible, they could be removed through an appropriate deconvolution process using the ultrasonic image information that can be provided by the present endoscopic system along with the photoacoustic image information, after carefully analyzing how the image artifacts are intervened into an obtained photoacoustic image in advance. The reason why those image artifacts could be filtered in this way is that the corresponding unwanted photoacoustic signals detected by the array transducer 1111, i.e., the photoacoustic waves generated by the transparent electrodes and then detected by the array transducer 1111 after being reflected from the object, is very similar to the ultrasonic pulse-echo signals acquired according to a specific ultrasound imaging mode (for example, the simultaneous excitation mode of all the transducer elements, i.e., parallel beamforming), in terms of the morphological pattern recorded in an image. Hence, as suggested in Prior Document 17, while photoacoustic image data are continuously recorded, if the mentioned specific ultrasound imaging mode is performed between every two successive photoacoustic image frames (i.e., the photoacoustic and the ultrasound image data are recorded alternately), the obtained ultrasound image information could be utilized as deconvolution data in a subsequent image processing procedure.

The PAE-EUS probe according to an embodiment may further include a backing layer 1111-B that is also transparent and is located between the light diffuser 1112 and the piezoelectric polymer film 1111-Piezo-Polymer. That is, as shown in FIG. 6, the backing layer 1111-B can be placed right underneath (i.e., along the −Z direction) the piezoelectric polymer film 1111-Piezo-Polymer, and the laser beam propagating from the light diffuser 1112 can freely pass through the backing layer 1111-B because the backing layer 1111-B is also transparent. Here, the backing layer 1111-B refers to a layer that may increase the sensitivity of the array transducer 1111 by providing an adequate acoustic impedance difference to the piezoelectric polymer film 1111-Piezo-Polymer, and it may also function as a sound absorbing layer that absorbs the remnant photoacoustic or ultrasonic waves that are not perfectly captured by the array transducer 1111 as a desired electric signal.

According to another embodiment, the backing layer 1111-B may be integrated with the light diffuser 1112 as a single unit. That is, in this case, the light diffuser 1112 may function as a backing layer as well as a sound absorbing layer. For example, a scattering light diffuser 1112OD that exhibits these characteristics could be implemented by adding acoustic scatterers and sound absorbers, such as epoxy or silica particles, into a light-diffusing material that serves as a substrate.

According to another embodiment, the backing layer 1111-B may be located right behind (i.e., along the −Z direction) the internal reflection coating layer 1112OD-RC, as seen in FIG. 3, or the light reflection mirror 1112OD-M, seen in FIG. 5, in the form of a thin layer. In this case, the backing layer 1111-B may function as a sound absorbing layer rather than as an acoustic matching layer because it does not directly contact the array transducer 1111.

Figure 7:
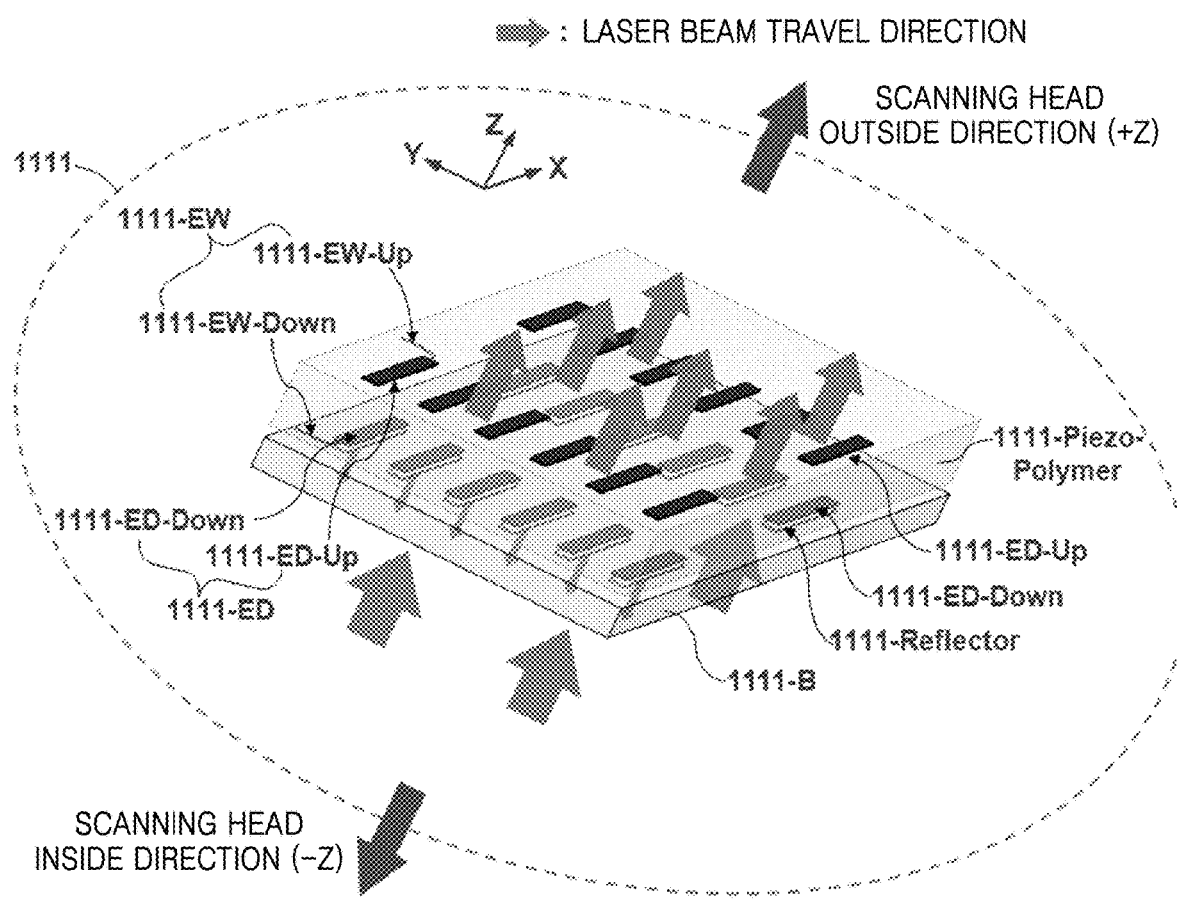
FIG. 7 is a view illustrating the structure of a portion of the array transducer implemented using a piezoelectric polymer film and non-transparent electrodes.
Figure 8A:
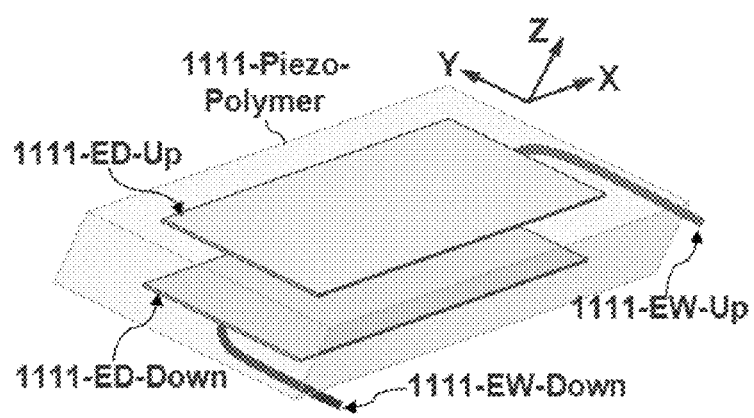
FIGS. 8A through 8D are views illustrating an input/output structure of the electric wires connected to each of the elements of the array transducer.
Figure 8B:
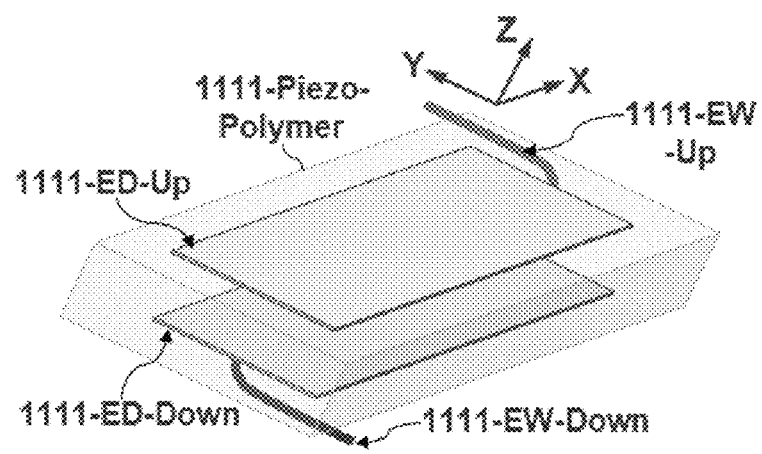
Figure 8C:
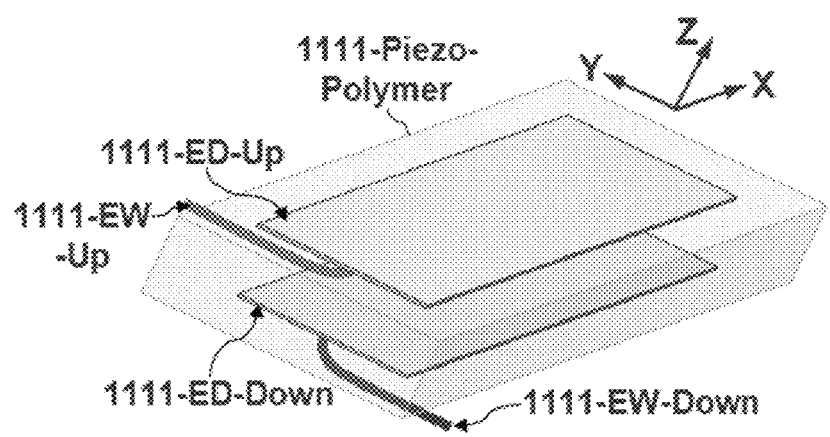
Figure 8D:
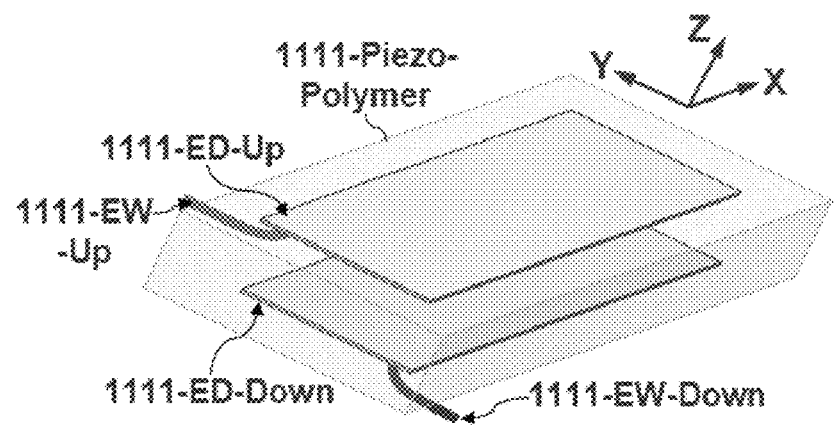

FIG. 7 is a view illustrating the structure of a portion of the array transducer 1111 implemented using a piezoelectric polymer film and non-transparent electrodes.

According to an embodiment, the multiple first electrodes 1111-ED-Up and the multiple second electrodes 1111-ED-Down may be formed as non-transparent electrodes.

Referring to FIG. 7, the electrodes 1111-ED may be non-transparent. In this case, the intervals between the first electrodes 1111-ED-Up and the intervals between the second electrodes 1111-ED-Down may be increased appropriately in order to provide an optical path through which a laser beam can freely pass. That is, although the electrodes 1111-ED are non-transparent, since the piezoelectric polymer film 1111-Piezo-Polymer itself is transparent, a laser beam can be transmitted through the portion where no electrode is distributed; thus, a partial transmission effect still can be achieved along the entire span area of the array transducer 1111.

Of course, in this case, an effective LEA may be reduced by the amount of the area occupied by the non-transparent electrodes. However, even in this case, a considerable amount of light energy can still be delivered through the LEA. For example, if only half of the electrodes shown in FIG. 6 are employed in an array transducer 1111, and all of them are formed as non-transparent electrodes (in which case, the final spacing between the electrodes will be increased, as shown in FIG. 7), about half of the energy corresponding to the case where all the electrodes depicted in FIG. 6 are transparent may be transmitted.

In addition to the loss of the LEA, performance degradation, such as lateral resolution degradation due to the loss of an USA, may be a concern in this embodiment. However, even in this case, since the total span area of all the transducer elements is not reduced, in comparison to the case depicted in FIG. 6 (that is, the total viewing angle for a point object formed by all the transducer elements is still the same), the lateral resolution performance is not significantly decreased.

According to an embodiment, a light reflection layer 1111-Reflector may be located between the second electrodes 1111-ED-Down and the light diffuser 1112. If the electrodes 1111-ED are non-transparent electrodes, the light reflection layers 1111-Reflector may also be placed right underneath (i.e., along the −Z direction) the second electrodes 1111-ED-Down. In this case, the light reflection layers 1111-Reflector prevent a laser beam from entering the electrodes 1111-ED. If no light reflection layer 1111-Reflector is provided, some amount of the laser beam may be absorbed by the electrodes 1111-ED due to the non-transparent characteristics of those electrodes; thus, the unwanted photoacoustic waves, which would act later as acoustic noise or image artifacts, may be generated by the electrodes 1111-ED. Hence, if the light reflection layers 1111-Reflector are formed right underneath the second electrodes 1111-ED-Down, as shown in FIG. 7, the problem mentioned above can be prevented, and a laser beam approaching the light reflection layer 1111-Reflector may be reflected back to the light diffuser 11112 and can be recycled.

As described above, in the embodiments shown in FIGS. 6 and 7, an array transducer 1111 is implemented by arranging multiple electrodes on both surfaces of the piezoelectric polymer film 1111-Piezo-Polymer. That is, although only a single piece of the piezoelectric polymer film 1111-Piezo-Polymer is employed, and it extends over the entire span area of the USA or the LEA like a wafer, due to the multiple electrodes 1111-ED formed on both surfaces of the piezoelectric polymer film 1111-Piezo-Polymer with a predetermined width and interval, it (or they) can function as an array transducer.

However, one important thing should be noted here: only the two electrodes 1111-ED that are placed at each side of the piezoelectric polymer film 1111-Piezo-Polymer and that face each, like a parallel-plate structure, can form a sensor pair unit that functions as a transducer element. In other words, if there is any spot where any two pieces of electrically-conducting materials face each other at the points located at opposite sides of the piezoelectric polymer film 1111-Piezo-Polymer, the spot can also function as an ultrasonic signal sensing area. Accordingly, electric wires connected to each transducer element have to be carefully designed and arranged.

FIGS. 8A through 8D are views illustrating the input/output structure of the electric wires connected to each of the elements of the array transducer 1111. Although the illustrated electric wire connections look random, there is a common rule that an electric wire 1111-EW-Up connected to the first electrode 1111-ED-Up and an electric wire 1111-EW-Down connected to the second electrode 1111-ED-Down should not face each other.

Until now, several embodiments of an optically transparent array transducer 1111, which can be implemented using a piezoelectric polymer film 1111-Piezo-Polymer, have been described, and, in the presented embodiments, it can be seen that only a single piece of piezoelectric polymer film, which spans the entire area of an USA or LEA, is employed. However, according to the present disclosure, an array transducer can also be embodied by using multiple pieces of piezoelectric polymer films, which are placed piecewise inside the array transducer (the related figure is not shown).

According to another embodiment of the present disclosure, the piezoelectric layer of an array transducer 1111 may be formed from a ceramic material or a single crystal-based piezoelectric material that is frequently utilized in an existing ultrasound imaging instrument. In the current ultrasound imaging field, representative examples of a ceramic-based piezoelectric material include lead zirconate titanate (PZT) and barium titanate, and representative examples of a single crystal-based piezoelectric material include lithium niobate (LiNbO$_3$) and lead magnesium niobate-lead titanate (PMN-PT) (hereinafter, the term "ceramic" and "single crystal" are all encompassed as "crystal").

In general, realizing an array transducer required for the present disclosure by using a crystal-based piezoelectric material may not be as simply as the case using the piezoelectric polymer film 1111-Piezo-Polymer because crystal-based piezoelectric materials do not have high optical transparency or high flexibility in comparison to polymer-based piezoelectric materials. However, even with the crystal-based piezoelectric materials, an array transducer that satisfies the described requirements can be formed by manufacturing individual transducer elements first and then arranging them in parallel at predetermined intervals.

Figure 9:
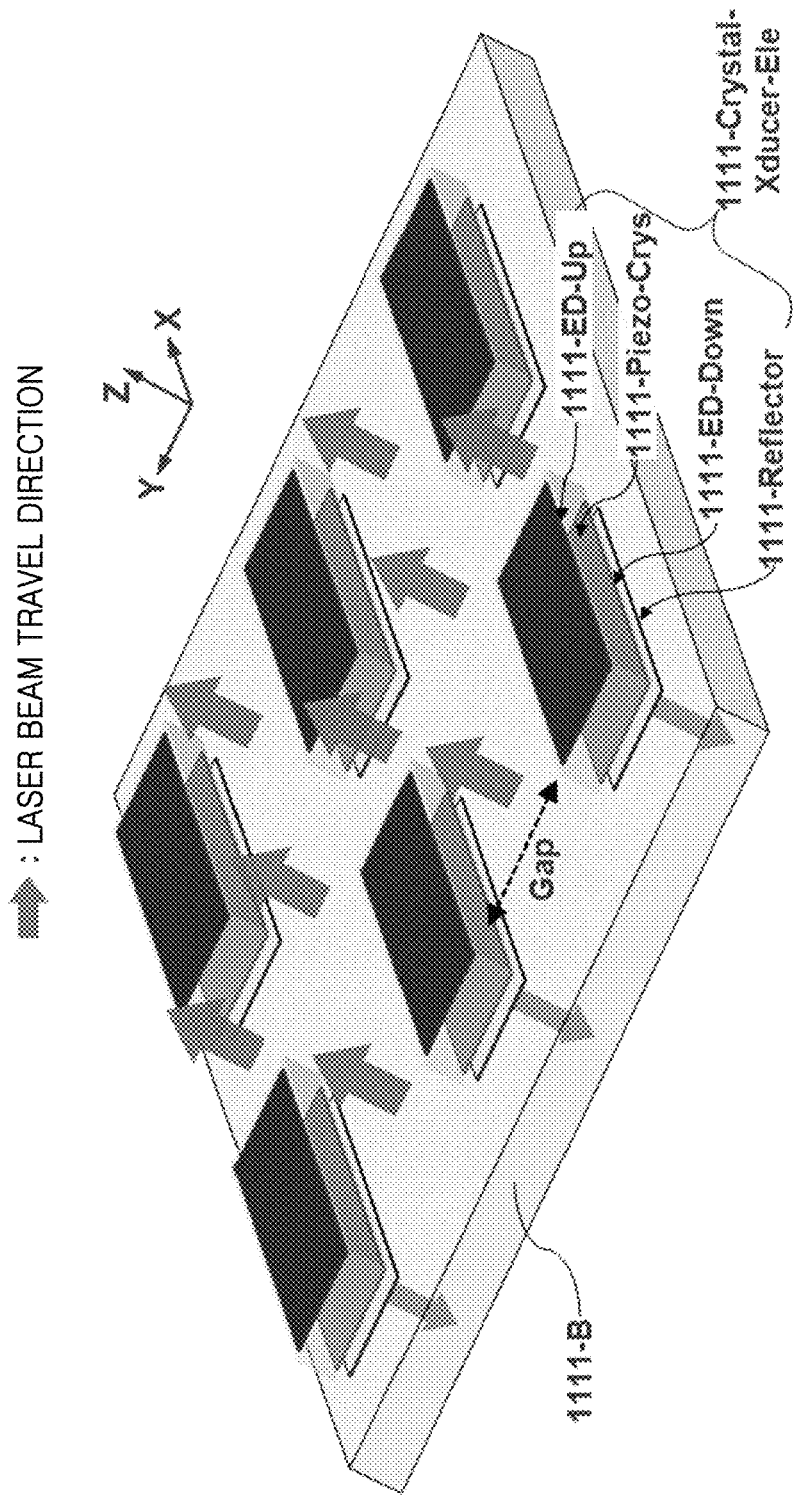
FIG. 9 is a view illustrating the structure of an optically-transparent array transducer implemented using a ceramic or crystal-based piezoelectric material.

FIG. 9 is a view illustrating the structure of an optically-transparent array transducer 1111 implemented based on the mentioned manufacturing procedure. Referring to FIG. 9, multiple transducer elements 1111-Crystal-Xducer-Ele, in which the electrodes 1111-ED and the electric wires 1111-EW (not shown) are previously formed on both surfaces of a piezoelectric crystal 1111-Piezo-Crys with piezoelectricity (i.e., prior machined), are arranged on the backing layer 1111-B, which is also optically transparent, at predetermined intervals to form an array transducer 1111. That is, even in this case, a laser beam propagating toward a target object to be examined can pass through the space (i.e., gaps) formed between the individual transducer elements 1111-Crystal-Xducer-Ele, as seen in the case presented in FIG. 7 (i.e., a partially transparent array transducer is formed). In this case, the gaps between the transducer elements 1111-Crystal-Xducer-Ele could be filled with the same material utilized to form the acoustic matching layer 1117 (e.g., TPX), or the gaps could be filled with another material. However, it is preferable that the type of material used to fill the gap be transparent.

Moreover, in this embodiment, the light reflection layers 1111-Reflector may be added right underneath (that is, −Z direction) the second electrodes 1111-ED-Down, as depicted in FIG. 7, in order to prevent a laser beam from penetrating into and passing through the second electrodes 1111-ED-Down.

Furthermore, in this embodiment, a backing layer 1111-B that functions as a base (substrate) for affixing the transducer elements 1111-Crystal-Xducer-Ele, as well as a sound absorber may be added. In addition, the backing layer 1111-B may enable the transducer elements 1111-Crystal-Xducer-Ele to exhibit maximum sensitivity performance by having an appropriate acoustic impedance difference in comparison to the piezoelectric crystals 1111-Piezo-Crys.

According to another embodiment, the backing layer 1111-B may be integrally formed with the light diffuser 1112 (that is, the light diffuser 1112 itself may function as a backing layer as well as a sound absorbing layer). In this case, all the transducer elements 1111-Crystal-Xducer-Ele are directly attached to a surface of the scattering light diffuser 1112OD.

Until now, several embodiments of an optically-transparent array transducer 1111 have been described. Hereinafter, structures showing how the electrical signal wires are connected to the array transducer 1111 are presented.

Figure 10A:
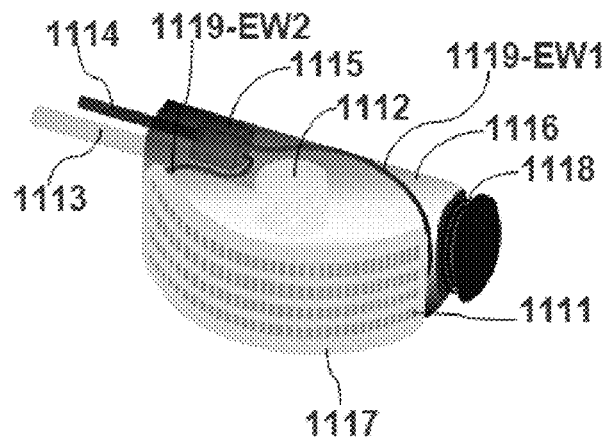
FIGS. 10A and 10B are views illustrating a wiring diagram of the electric signal wires of the array transducer inside a scanning head.
Figure 10B:
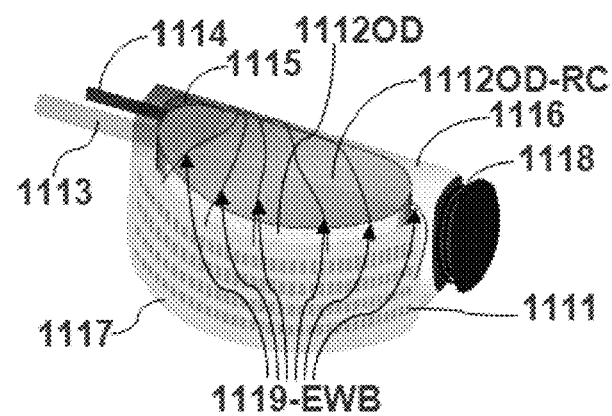

FIGS. 10A and 10B are views illustrating a wiring diagram of the electric signal wires of the array transducer 1111 inside the scanning head 1110. Whether the light diffuser 1112 embodied with only a small lens and a mirror (as seen in FIG. 10A) or the scattering light diffuser 1112OD with a large volume (as seen in FIG. 10B) is employed for the light diffuser 1112, it is preferable that a number of local electric wire bundles 1119-EW1, 1119-EW2, and 1119-EWB exiting the transparent array transducer 1111 be arranged around the sides of the light diffuser 1112 and connected to the first hub 1115 along the right inner space of the scanning head casing 1116 to avoid interference with the laser beam's path.

Figure 11:
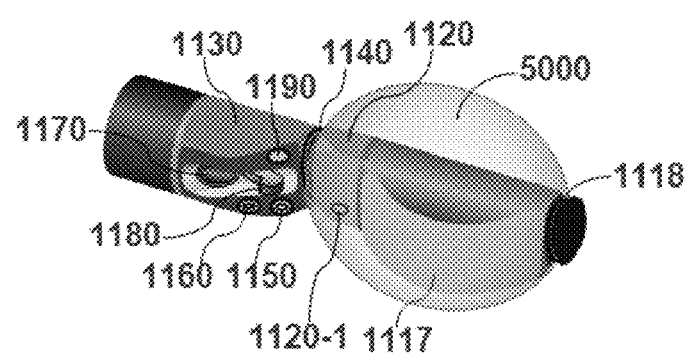
FIG. 11 is a view for explaining an exemplary embodiment of a balloon installed on an end of a probe in order to solve an acoustic matching problem between an object to be examined and the probe during an endoscopic imaging procedure.
Figure 12:
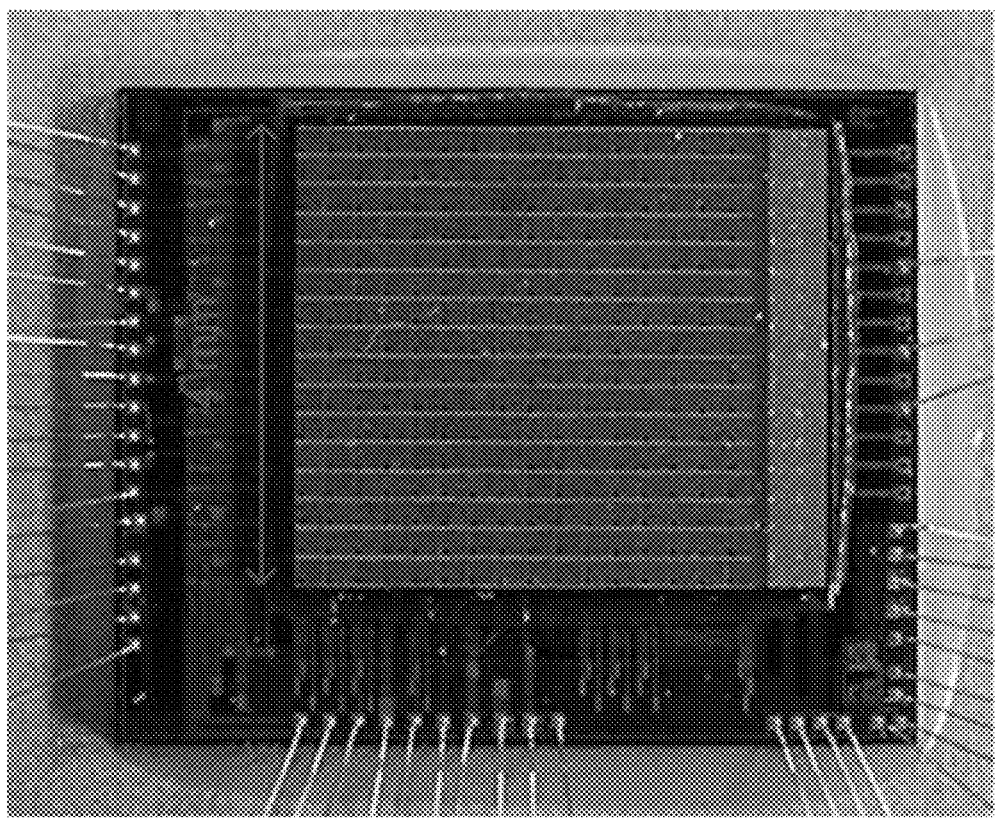
FIGS. 12 through 16 are views illustrating the endoscopic structures of Prior Documents 9 through 15.
Figure 13:
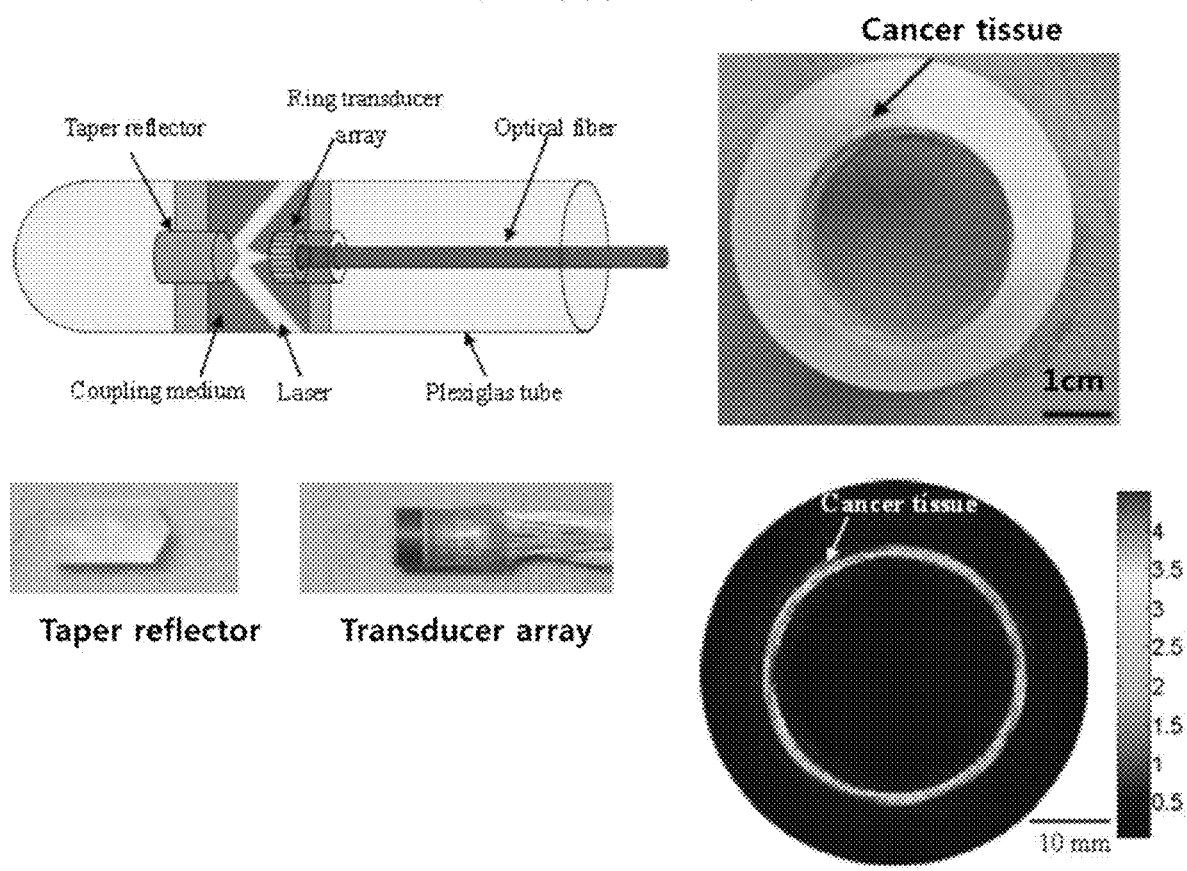
Figure 14:
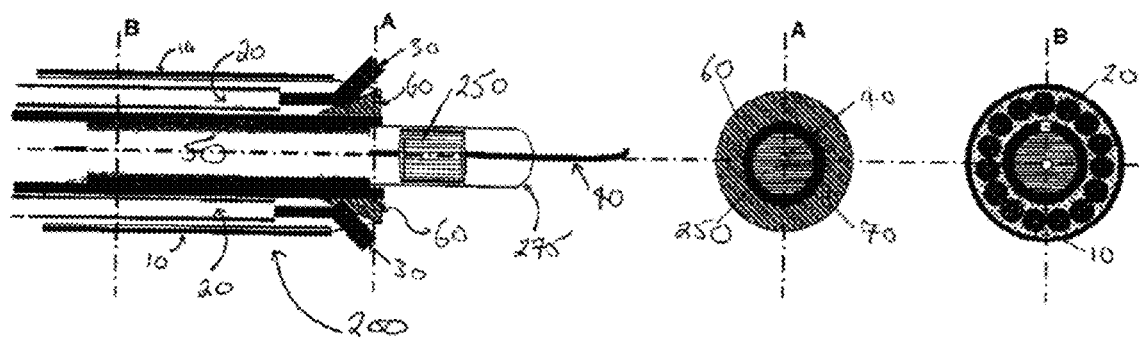
Figure 15:
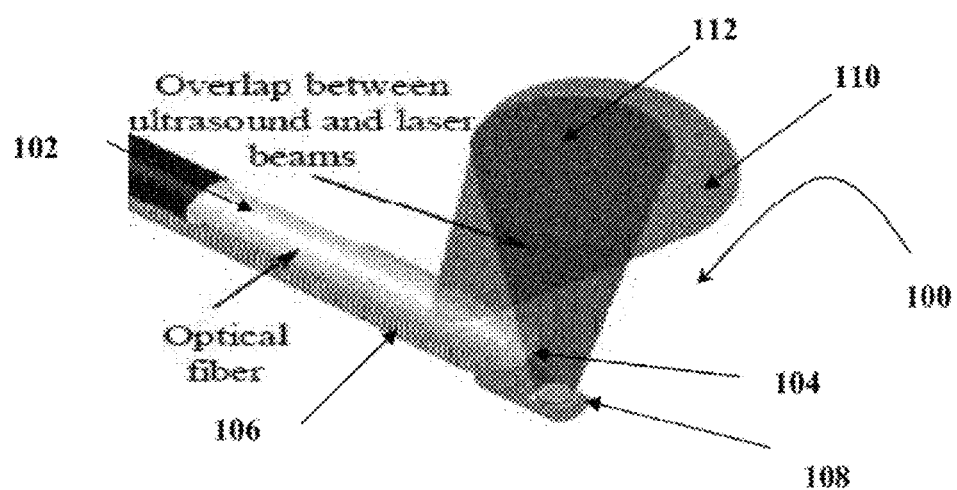
Figure 16:
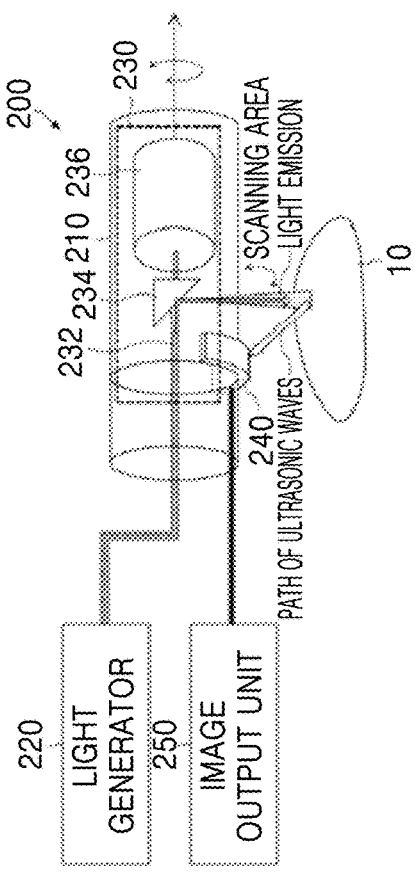
Figure 16:
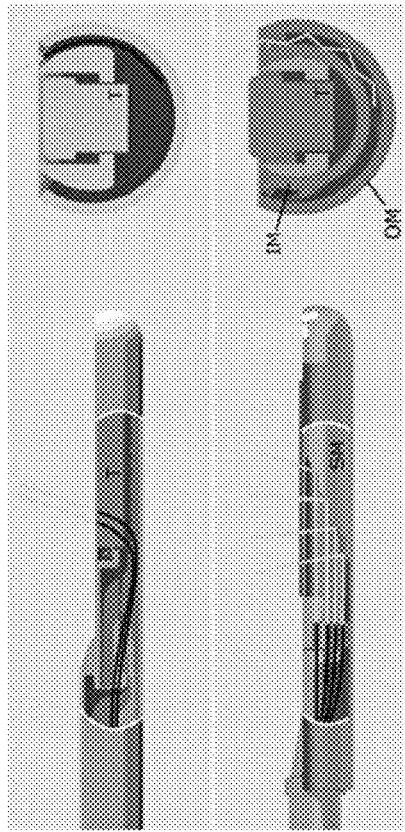
Figure 16:
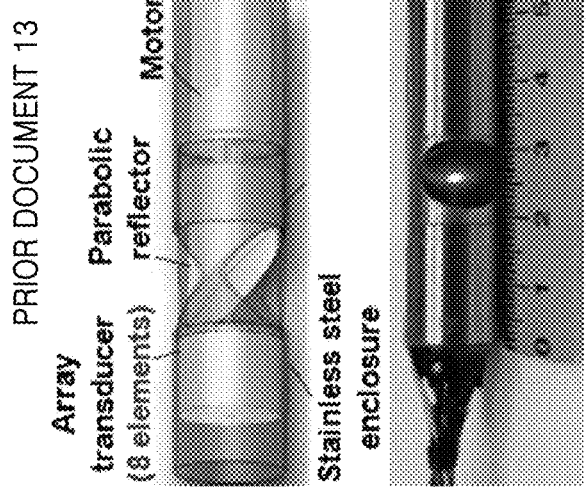

FIG. 11 is a view illustrating an exemplary embodiment of a balloon installed on an end of a probe in order to solve an acoustic matching problem between an object to be examined and the probe during an endoscopic imaging procedure. Since the present endoscopic system obtains a signal by means of ultrasonic waves, as it does in existing EUS systems, the same balloon contact method that is currently utilized in EUS can also be used. To this end, the scanning head 1110 may be entirely surrounded by a balloon 5000, and water may be injected into the balloon 5000 through a very small fluid injection hole 1120-1 formed around the second groove for balloon fixation 1140, located between the scanning head base frame 1120 and the hose end frame 1130 or at any spot formed on the scanning head base frame 1120.

Until now, a principlefor obtaining photoacoustic-ultrasonic dual-mode 2D or 3D tomographic images using the endoscopic system provided by the present disclosure has been described. However, if necessary, proposed concepts may be implemented in such a system embodiment that only obtains partial image information (e.g., photoacoustic image only). Moreover, in the configuration and arrangement of the subsystems shown in FIG. 1, some of the elements may be integrated into a single physical unit, and the spatial positions of some of the elements may be changed appropriately. For example, the laser source 2000 could be integrated with the system console 4000, and various cables, such as the probe-console communication cable 1700, the transducer data cable 1800, and the guiding optical fiber cable 1900 that are connected to the base of the PAE-EUS probe 1000, may also be integrated into a single cable.

In the present disclosure, a detailed system concept and probe structurefor solving the mismatch issue between an LEA and a USA and the limited imaging depth issue of prior inventions has been described, as have several exemplary embodiments.

In general, the main reason for utilizing such an array transducer-based electronic scanning mechanism in GI endoscopy is to achieve a large-depth imaging performance. However, prior inventions have shown a fundamental limit in terms of this performance due to the aforementioned problems. In contrast, the present disclosure could successfully solve those problems by using the light diffuser 1112 and the optically-transparent array transducer 1111 concepts; the present disclosure also presented a very detailed system structure for applying the proposed concepts to GI endoscopy, for which no other prior invention has suggested any detailed system configuration.

The main reason that the present disclosure could successfully achieve a large-depth imaging performance within a limited probe size, which has been the biggest technical challenge in the PAE field, is because the LEA and the USA of the scanning head overlap each other by employing an array transducer 1111 with optical transparency. Moreover, due to the concept, the mismatch issue between an IA and an SA of prior inventions could be solved simultaneously.

As described above, according to an embodiment, the mismatch issue between an IA and an SA of prior PAE systems may be solved, and much more light energy can be delivered than is possible with prior inventions; thus, the maximum imaging depth of a PAE system may be greatly increased up to the theoretical limit that is determined by the ANSI safety regulation (i.e., Prior Documents 16). However, the scope of the present disclosure is not limited by the effect.

While one or more embodiments have been described with reference to the figures, it will be understood by those of ordinary skill in the art that various changes in form and details may be made therein without departing from the spirit and scope of the disclosure as defined by the following claims.

What is claimed is:

1. A photoacoustic-ultrasonic endoscope comprising:
    an optical fiber placed along an inside of an insertion hose of an endoscope probe;
    a light diffuser provided so that a laser beam guided and emitted from the optical fiber is diffused and finally emitted toward a target point of an object to be examined through a partial surface allocated at a side of the light diffuser in such a way that the partial surface does not overlap an original propagation direction of the laser beam emitted from the optical fiber; and
    a one or two-dimensional optically-transparent array transducer that passes the diffused laser beam and also fires ultrasonic pulses and detects ultrasonic waves generated from the object to be examined by being disposed on the partial surface of the light diffuser,
    wherein an outer surface other than the partial surface of the light diffuser is coated or surrounded by a light reflecting layer that reflects back a light scattered from the light diffuser into an interior of the light diffuser so that scattered and reflected light can be eventually emitted outside only through the partial surface by the light diffuser.

2. The photoacoustic-ultrasonic endoscope of claim 1, wherein the laser beam diffused by the light diffuser passes through an entire area of the array transducer.

3. The photoacoustic-ultrasonic endoscope of claim 1, further comprising an acoustic matching layer covering at least a part of an outer surface of the array transducer and comprising a material through which light is transmitted.

4. The photoacoustic-ultrasonic endoscope of claim 3, wherein the material of the acoustic matching layer is made to comprise polymethylpentene (TPX).

5. The photoacoustic-ultrasonic endoscope of claim 1, wherein a light emitting area (LEA) where the diffused laser beam escapes from the array transducer and an ultrasonic sensor area (USA) where the array transducer senses ultrasonic waves overlap each other.

6. The photoacoustic-ultrasonic endoscope of claim 1, wherein the light diffuser has a shape in which the partial surface is convex outward.

7. The photoacoustic-ultrasonic endoscope of claim 1, wherein a reduced scattering coefficient ($\mu_s'$) of the light diffuser is equal to or greater than 0.1 $cm^{-1}$ and equal to or less than 1.0 $cm^{-1}$ or
    a distance from a distal end of the optical fiber from which the laser beam is emitted to the center of the optical diffuser coincides with a transport average free path value of the optical diffuser.

8. The photoacoustic-ultrasonic endoscope of claim 1, wherein the light diffuser comprises at least one of polypropylene, plastic resin, ground glass, and engineered diffuser.

9. The photoacoustic-ultrasonic endoscope of claim 1, wherein a distal end of the optical fiber from which the laser beam is emitted is inserted into the light diffuser to a certain depth.

10. The photoacoustic-ultrasonic endoscope of claim 1, wherein the light diffuser has an empty space, and an end point of the optical fiber is located in the empty space.

11. The photoacoustic-ultrasonic endoscope of claim 10, wherein the empty space has a conical shape.

12. The photoacoustic-ultrasonic endoscope of claim 1, further comprising a light reflection mirror surrounding an outer surface of the light diffuser, wherein the light reflection mirror has an opened portion corresponding to the partial surface in order to emit the laser beam diffused by the light diffuser only through the partial surface.

13. The photoacoustic-ultrasonic endoscope of claim 1, wherein the array transducer comprises:
    a piezoelectric layer having a predetermined thickness;
    a plurality of first electrodes located on a first surface of the piezoelectric layer a one-dimensional (1D) or two-dimensional (2D) array; and
    a plurality of second electrodes located on a second surface of the piezoelectric layer opposite to the first surface and in parallel to the plurality of first electrodes,
    wherein the array transducer passes the laser beam through at least a partial area.

14. The photoacoustic-ultrasonic endoscope of claim 13, further comprising a transparent backing layer between the light diffuser and the piezoelectric layer.

15. The photoacoustic-ultrasonic endoscope of claim 13, wherein the plurality of first electrodes and the plurality of second electrodes are transparent electrodes.

16. The photoacoustic-ultrasonic endoscope of claim 15, wherein each of the plurality of first electrodes and the plurality of second electrodes comprises any one selected from the group consisting of indium tin oxide (ITO), indium zinc oxide (IZO), zinc oxide (ZnO), indium oxide ($In_2O_3$), Ge-doped $In_2O_3$ (IGO), and aluminum-doped zinc oxide (AZO).

17. The photoacoustic-ultrasonic endoscope of claim 13, wherein the plurality of first electrodes and the plurality of second electrodes comprise non-transparent electrodes.

18. The photoacoustic-ultrasonic endoscope of claim 17, further comprising a light reflection layer between the plurality of second electrodes and the light diffuser.

19. A photoacoustic-ultrasonic endoscope comprising:
    an optical fiber placed along an inside of an insertion hose of an endoscope probe;
    a light diffuser provided so that a laser beam guided and emitted from the optical fiber is diffused and finally emitted toward a target point of an object to be examined through a partial surface allocated at a side of the light diffuser in such a way that the partial surface does not overlap an original propagation direction of the laser beam emitted from the optical fiber: and a one or two-dimensional optically-transparent array transducer that passes the diffused laser beam and also fires ultrasonic pulses and detects detect ultrasonic waves generated from the object to be examined by being disposed on the partial surface of the light diffuser, wherein an outer surface other than the partial surface of the light diffuser is coated or surrounded by a light reflecting layer that reflects back a light scattered from the light diffuser into an interior of the light diffuser so that scattered and reflected light can be eventually emitted outside only through the partial surface by the light diffuser, wherein a light emitting area (LEA) where the diffused laser beam escapes from a scanning head and an ultrasonic sensor area (USA) of the array transducer overlap each other.

* * * * *